United States Patent
Slayton et al.

(10) Patent No.: US 10,143,861 B2
(45) Date of Patent: Dec. 4, 2018

(54) SYSTEM AND METHOD FOR NON-INVASIVE TREATMENT WITH IMPROVED EFFICIENCY

(71) Applicant: Guided Therapy Systems, LLC, Mesa, AZ (US)

(72) Inventors: Michael H. Slayton, Tempe, AZ (US); Peter G. Barthe, Phoenix, AZ (US)

(73) Assignee: Guided Therapy Systems, LLC, Mesa, AZ (US)

( * ) Notice: Subject to any disclaimer, the term of this patent is extended or adjusted under 35 U.S.C. 154(b) by 82 days.

(21) Appl. No.: 14/569,001

(22) Filed: Dec. 12, 2014

(65) Prior Publication Data

US 2015/0165238 A1 Jun. 18, 2015

Related U.S. Application Data

(60) Provisional application No. 61/915,519, filed on Dec. 13, 2013, provisional application No. 62/047,633, filed on Sep. 8, 2014.

(51) Int. Cl.
*A61H 1/00* (2006.01)
*A61N 7/00* (2006.01)
(Continued)

(52) U.S. Cl.
CPC .......... *A61N 7/00* (2013.01); *A61B 18/18* (2013.01); *A61B 18/1815* (2013.01); *A61H 15/0085* (2013.01); *A61H 15/0092* (2013.01); *A61H 15/02* (2013.01); *A61H 23/0245* (2013.01); *A61N 7/02* (2013.01); *A61B 18/12* (2013.01); *A61B 18/203* (2013.01); *A61B 2017/00075* (2013.01); *A61B 2018/00458* (2013.01); *A61B 2018/1807* (2013.01); *A61B 2090/065* (2016.02); *A61H 2015/0014* (2013.01); *A61H 2201/0176* (2013.01); *A61H 2201/0184* (2013.01); *A61H 2201/105* (2013.01);
(Continued)

(58) Field of Classification Search
CPC .............................. A61N 7/00; A61H 23/0245
See application file for complete search history.

(56) References Cited

U.S. PATENT DOCUMENTS 5,641,909 A * 6/1997 Kiefer ................ G01N 29/0672
73/623
2008/0195182 A1 8/2008 Fertner
(Continued)

FOREIGN PATENT DOCUMENTS

EP 0637442 A1 2/1995
WO 2011/034122 A1 3/2011

*Primary Examiner* — Hien Nguyen
(74) *Attorney, Agent, or Firm* — Quarles & Brady LLP

(57) ABSTRACT

This disclosure provides systems and methods for non-invasive treatment to a region of interest with improved efficiency. The systems and methods can include a treatment device having an energy source and a rolling member. The rolling member can include a wall disposed between the energy source and the region of interest. Treatment can be provided at a first location, followed by moving the treatment device, then energy transmission can be terminated if coupling between the energy source and the region of interest is interrupted or treatment can be provided at a second location if the coupling between the energy source and the region of interest is uninterrupted.

21 Claims, 17 Drawing Sheets

(51) Int. Cl.
*A61B 18/18* (2006.01)
*A61H 15/02* (2006.01)
*A61N 7/02* (2006.01)
*A61H 23/02* (2006.01)
*A61B 18/12* (2006.01)
*A61B 17/00* (2006.01)
*A61B 18/00* (2006.01)
*A61B 18/20* (2006.01)
*A61N 5/06* (2006.01)
*A61H 15/00* (2006.01)
*A61B 90/00* (2016.01)

(52) U.S. Cl.
CPC ........... *A61H 2201/1685* (2013.01); *A61H 2201/1695* (2013.01); *A61H 2201/5028* (2013.01); *A61H 2201/5038* (2013.01); *A61H 2201/5046* (2013.01); *A61H 2201/5064* (2013.01); *A61H 2201/5082* (2013.01); *A61H 2201/5092* (2013.01); *A61N 5/0616* (2013.01); *A61N 2007/006* (2013.01); *A61N 2007/0034* (2013.01); *A61N 2007/0078* (2013.01)

(56) References Cited

U.S. PATENT DOCUMENTS

| | | | |
|---|---|---|---|
| 2010/0160782 A1* | 6/2010 | Slayton | A61B 5/4869 600/439 |
| 2011/0238085 A1* | 9/2011 | Berzak | A45D 26/00 606/133 |
| 2013/0103017 A1 | 4/2013 | Weckwerth | |
| 2015/0142087 A1* | 5/2015 | Jurna | A61N 1/328 607/99 |

* cited by examiner

SYSTEM AND METHOD FOR NON-INVASIVE TREATMENT WITH IMPROVED EFFICIENCY

CROSS-REFERENCE TO RELATED APPLICATIONS

This application is based on, claims priority to, and incorporates herein by reference for all purposes, U.S. Provisional Patent Application No. 61/915,519, filed Dec. 13, 2013, and U.S. Provisional Patent Application No. 62/047,633, filed Sep. 8, 2014.

BACKGROUND

Current ultrasound methods for treatment of a targeted media, including live tissue and soft tissue, are limited to a small treatment area. This is due to limitations in ultrasound technology, which limits the speed of treatment.

SUMMARY

The present disclosure overcomes the aforementioned drawbacks by presenting systems and methods for treating an area using ultrasound with increased speed and greater efficiency.

In one aspect, this disclosure provides a treatment device for delivering an energy into a region of interest beneath a target surface. The treatment device can include an energy source, a rolling member, a control module, a contact sensor, and a housing. The energy source can be configure for delivery of the energy. The rolling member can move the treatment device relative to the target surface. The rolling member can include a wall disposed between the energy source and the region of interest. The energy can pass through the wall at least once prior to the delivery into the region of interest. The control module can be configured to control the energy source. The contact sensor can be in communication with the control module and configure to determine when the energy source is coupled to the region of interest. The housing can be coupled to the rolling member to move along the target surface while retaining coupling between the energy source and the region of interest.

In another aspect, this disclosure provides a method of treating a first location and a second location within a region of interest beneath a target surface by delivery of an energy. The method can include one or more of the following steps: transmitting the energy, provided by an energy source of a treatment device, through at least one wall of a rolling member of the treatment device and into the first location; sensing, using a contact sensor of the treatment device, a coupling between the energy source and the region of interest; moving the treatment device relative to the target surface; and either: terminating the energy transmission if the coupling between the energy source and the region of interest is interrupted; or transmitting the energy, provided by the energy source, through the at least one wall of the rolling member and into the second location if the coupling between the energy source and the region of interest is uninterrupted.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Before the present invention is described in further detail, it is to be understood that the invention is not limited to the particular embodiments described. It is also to be understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

Specific structures, devices, and methods relating to improved ultrasound treatment efficiency and operation are disclosed. It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements.

Figure 1:
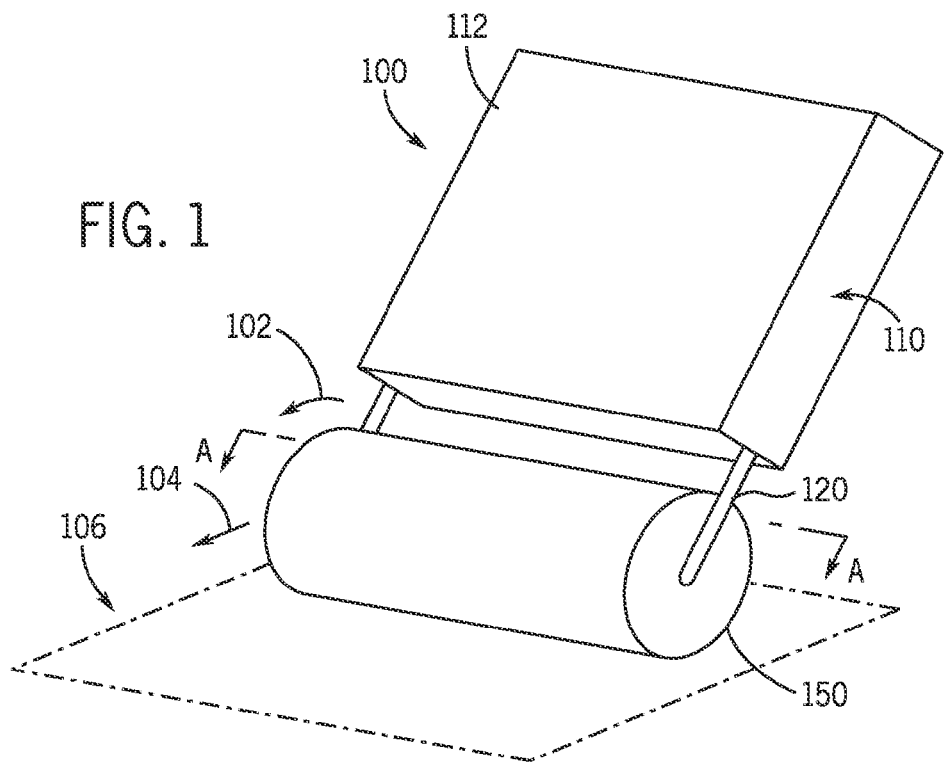
FIG. 1 is a perspective view illustrating an exemplary treatment device, according to one aspect of the present disclosure.

With reference to FIG. 1, a treatment device 100 is illustrated, in accordance with the present disclosure. The treatment device 100 can include a control module 110 and a transducer module 150. At least one linkage 120 can couple the transducer module 150 to the control module 110. The linkage 120 can provide an electronic interface between transducer module 150 and the control module 110. The transducer module 150 can be configured to contact a target surface 106. The treatment device 100 can be configured to treat a region of interest ("ROI") 108, such as, for example, a ROI 108 below the target surface 106. The treatment device 100 can include a housing 112. The housing 112 can be configured to encase the control module 110. The treatment device 100 can move in a forward direction 104, which can rotate the transducer module 150 in a rotational direction. The treatment device 150 can move in either direction, forward or back, and can move in an arcing motion or essentially a straight line. The treatment device 100 can move in response to an external force, such as a user or a robotic implement pushing or pulling the treatment device 100, or an internal force, such as a drive motor coupled to one or more wheels.

Figure 2:
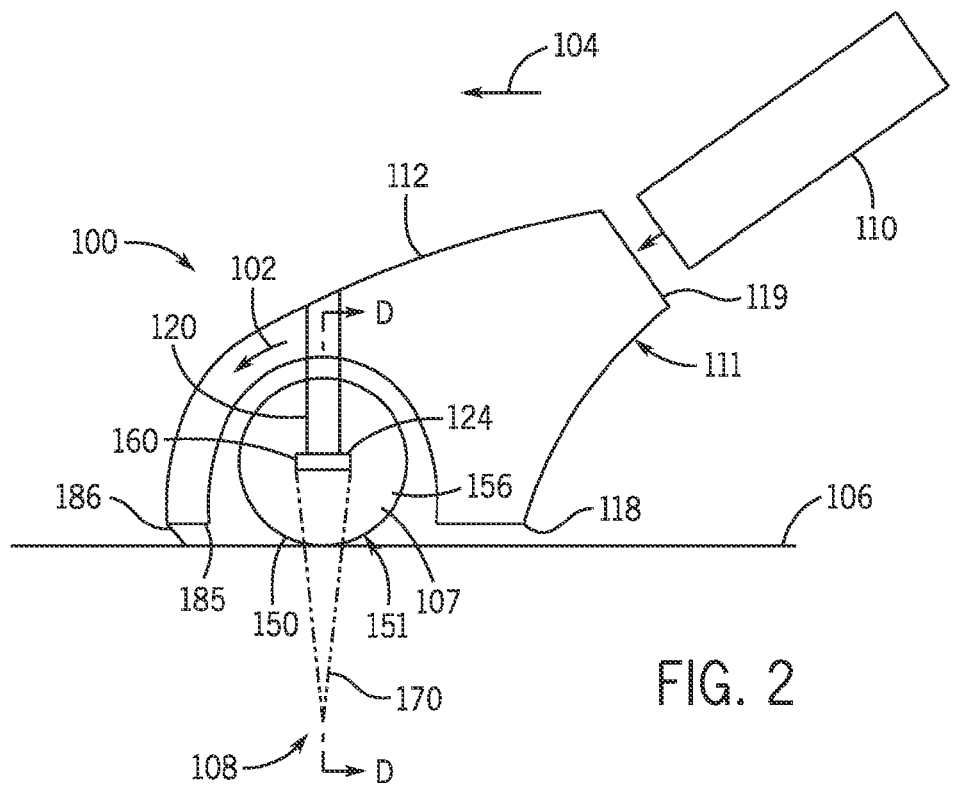
FIG. 2 is a side view illustrating an exemplary treatment device, according to one aspect of the present disclosure.
Figure 3:
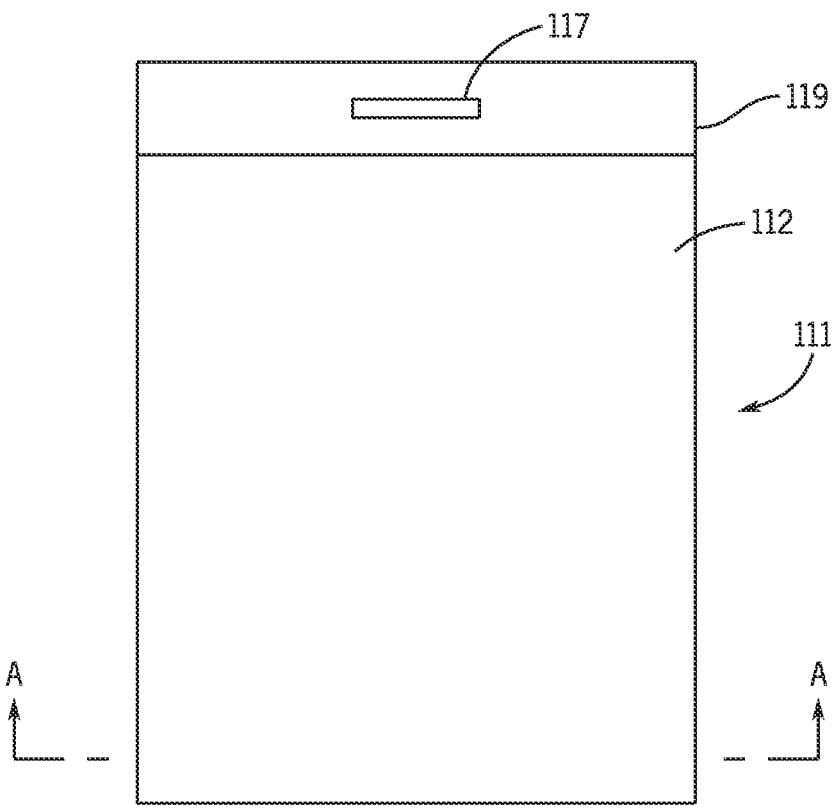
FIG. 3 is a top view illustrating the exemplary treatment device of FIG. 2, according to one aspect of the present disclosure.

Another exemplary treatment device 100 is illustrated in FIGS. 2 and 3. The treatment device 100 can include a transducer module 150, which can include at least one energy source 160. The transducer module 150 can be attached to the housing 112 and can be configured to rotate in a rotational direction 102 within the housing 112 while remaining coupled to the treatment surface 106. An axle 124 can be positioned through the center axis of the cylinder and can connect the transducer module 150 to the housing 112. In some embodiments, the axle 124 can include at least one energy source 160 configured to provide energy 170 to the ROI 108. The cylinder can be sealed to form an internal volume 156 that can contain a coupling medium 107 configured to facilitate coupling of the energy source 160 with tissue in the ROI 108. In some examples, the energy source 160 is at least one ultrasound transducer configured to controllably direct acoustic energy 170 into the ROI 108.

According to this example, the treatment device 100 includes an interface 117 configured to accept the portable device and provide communication between the portable device and a treatment module 111. The treatment module 111 can include an inset 119 to hold the portable device while interfaced with the treatment device 111. The treatment module 111 can include a guide 118 to position the treatment module 111 at a correct angle to target the energy 170 into the ROI 108. A second guide 185 can balance the system 100 in the correct treatment position. A bias member 186 can provide some resistance to help balance the system 100. Any of the embodiments of treatment device 100 can be configured with a guide 118 configured position the treatment device 100 at a desired angle to target the energy 170 into the ROI 108.

The control module 110 can be configured to receive at least one communication and control a distribution of the acoustic energy 170 transmitted by the energy source 160, such as, for example, an acoustic transducer. The control module 110 can be configured to receive a treatment start signal and a treatment stop signal. The control module 110 can be programmed to provide treatment to a ROI 108 for a desired outcome. The control module 110 can initiate and run a treatment program (treatment function), which can include the control of spatial parameters and/or temporal parameters of the energy source 160, to provide programmed distribution energy 170 in the ROI 108. The control module 110 can be configured to receive feedback from one or more sensors and/or detectors, and the control module 110 can terminate the treatment program based on the feedback. For example, it can terminate the delivery of energy if the position of the treatment device is outside a pre-defined area of treatment. Other examples will be provided hereinafter.

Figure 4:
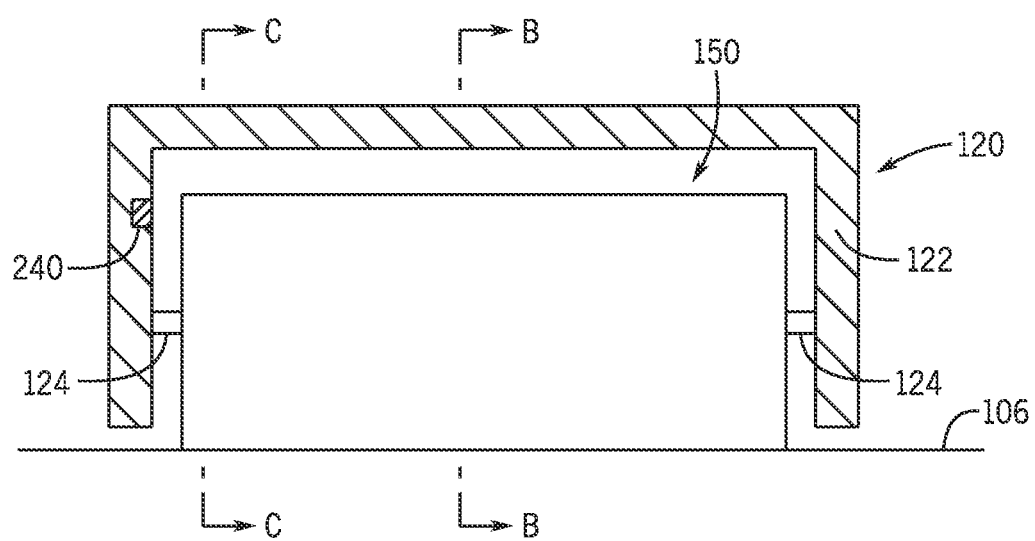
FIG. 4 is a front view illustrating a transducer module, according to one aspect of the present disclosure.

Referring now to FIG. 4, a front view of the transducer module 150 is illustrated, in accordance with one configuration. The transducer module 150 can include an axle 124. The linkage 120 can include a strut 122, which can be configured to provide structure to linkage 120. The linkage 120 can be coupled to the axle 124. In some embodiments, the linkage 120 can be configured for removal and attachment of the transducer module 150. In other embodiments, the linkage 120 can be configured to be permanently coupled to transducer module 150. The linkage 120 can include a coupling configured to engage the axle 124.

The linkage 120 can be an electronic interface between the control module 110 and the transducer module 150. For example, the strut 122 can be hollow and configured for wiring to run inside of the strut 122. In some examples, the strut 122 can be configured with a channel along a length of strut 122 for wiring to run inside of the channel in the strut 122. The strut 122 can include a thin film electrode configured to provide an electronic interface between the control module 110 and the transducer module 150. In some configurations, the strut 122 can include a position sensor 240.

The treatment device 100 can include a position sensor 240 in communication with the control module 110 and configured to monitor a position of the transducer module 150 and to calculate a speed of the rotation in the rotational direction 102 of the transducer module 150. In some configurations, the transducer module 150 can include the position sensor 240. The position sensor 240 can be integrated into the transducer module 150 or attached to the transducer module 150. The position sensor 240 can be configured to measure movement of the transducer module 150. For example, the position sensor 240 can calculate a distance traveled (delta distance or distance change) along the target surface 106. For example, the position sensor 240 may determine a speed of movement of the transducer module 150 and determine if the speed is within programmed limitations for providing treatment. For example if the speed is beyond a desired or effective speed, the position sensor 240 can provide a signal indicating the speed or an alert or other information to indicate the over-speed condition. The over-speed condition can be provided to a user and/or to a control module 110 to control, adjust, or stop emitting the therapeutic ultrasound energy 170.

In some configurations, the position sensor 240 can be programmed to determine a distance between pulses of therapeutic ultrasound energy 170 to create a plurality of treatment zones that are evenly spaced or can be disposed in any spatial configuration in one-, two-, or three-dimensions. As the transducer module 150 is moved in the direction 104, the position sensor 240 determines distance, regardless of a speed that the transducer module 150 is moved, at which a pulse of the therapeutic ultrasound energy 170 is to be emitted into ROI 108, as programmed into the control module 110. In some configurations, the transducer module 150 is triggered automatically via a timer and in combination with the position sensor 240 to assure movement of the transducer module 150.

The control module 110 can terminate the distribution of the acoustic energy 170 into the ROI 108, if the speed of the rotation in the rotational direction 102 of the transducer module 150 is below a minimum speed. The control module 110 can terminate the distribution of the acoustic energy 170 into the ROI 108, if the speed of the rotation in the rotational direction 102 of the transducer module 150 is above a desired or effective speed. As another non-limiting example, the control module 110 can terminate the distribution of the acoustic energy 170 into the ROI 108, if the direction of the rotation 102 of the transducer module 150 is changed.

Various sensing and monitoring components may also be implemented within control module 110. For example, monitoring, sensing, and interface control components may be capable of operating with the motion detection system implemented within the transducer module 150, to receive and process information such as acoustic or other spatial and temporal information from the ROI 108. Sensing and monitoring components may also include various controls, interfacing, and switches and/or power detectors. Such sensing and monitoring components may facilitate open-loop and/or closed-loop feedback systems within the treatment device 100.

In some configurations, sensing, and monitoring components may further include a sensor that may be connected to an audio or visual alarm system to signal overuse or impending overuse of the system. In this configuration, the system may be capable of determining the amount of energy transferred to the skin, and/or the time that the treatment device 100 has been actively emitting the energy 170. When a certain time or energy or temperature threshold has been reached, the alarm may sound an audible alarm, or cause a visual indicator to activate to alert the user that a threshold has been reached. This may control against overuse of the treatment device 100. In some configurations, the sensor may be operatively connected to the control module 110 and force the control module 110 to stop emitting the therapeutic ultrasound energy 170 from the transducer module 150.

Figure 5A:
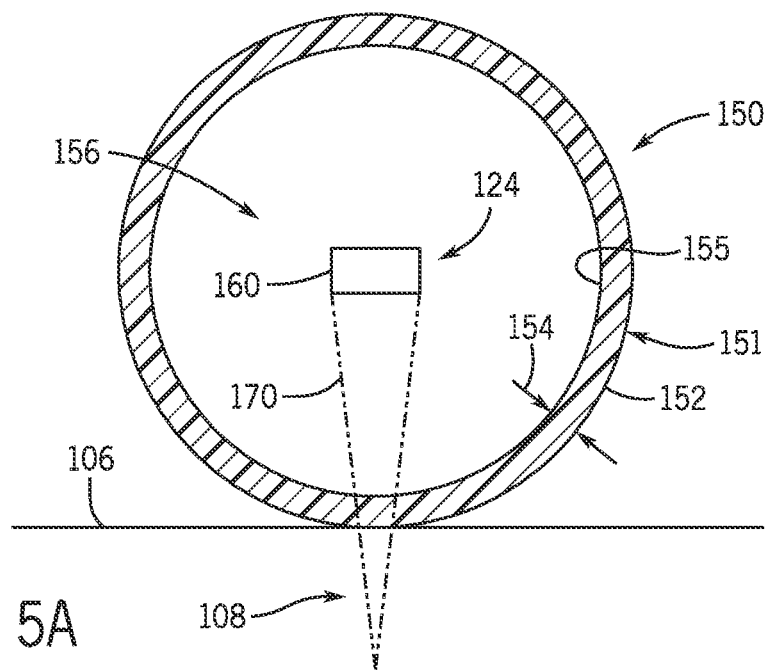
FIG. 5A provides one example of a cross-sectional view along the line B-B of FIG. 4, according to one aspect of the present disclosure.

Now referencing FIG. 5A, a cross-sectional view, along the line B-B of FIG. 4, of the transducer module 150 is illustrated in accordance with various aspects of the disclosure. The transducer module 150 can include a transducer module wall 151 having an outer surface 152 and an inner surface 155. The transducer module wall 151 has a thickness 154, which is a distance measured perpendicularly from the outer surface 152 to the inner surface 155. In various configurations, the thickness 154 can be configured to provide various physical attributes to ultrasound energy 170, as further discussed herein. The transducer module 150 can be configured to have an internal volume 156, which is bordered or bounded by the inner surface 155. The internal volume 156 can be filled with a coupling medium, as discussed herein. An axle 124 can be located at approximately a center point of a circumference as defined by the inner surface 155. The transducer module 150 can rotate around the axle 124, which can be stationary relative to an external frame. Alternatively, the transducer module 150 can be stationary relative to the axle 124, and the transducer module 150 and the axle 124 can rotate relative to a stationary external frame.

In some configurations, the axle 124 can include an energy source 160. The axle 124 can be configured to include the energy source 160 as a portion of a structure of the axle 124. The energy source 160 can be configured to emit energy 170 into the ROI 108 below the target surface 106 over a programmed period of time.

Figure 5B:
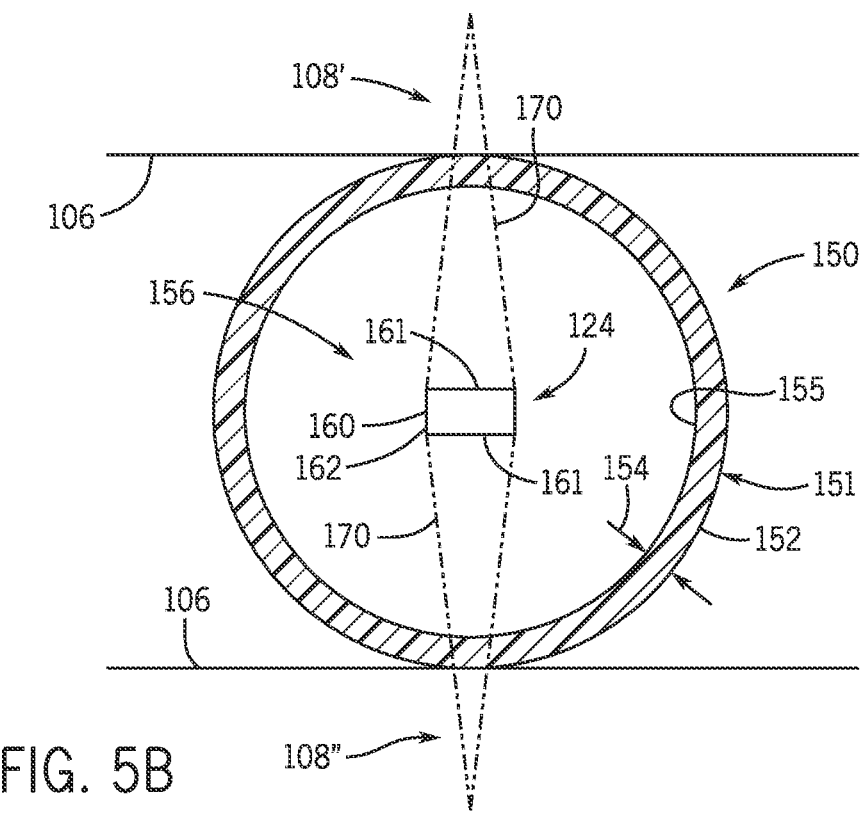
FIG. 5B provides another example of a cross-sectional view along the line B-B of FIG. 4, according to one aspect of the present disclosure.

FIG. 5B is a cross-sectional view, along the line B-B of FIG. 4, illustrating another example of the transducer module 150, in accordance with various configurations. As discussed herein, the axle 124 can include an energy source 160. The axle 124 can be configured to include the energy source 160 as a portion of a structure of the axle 124. As illustrated in FIG. 5B, the energy source 160 can be configured to emit energy 170 in two opposite directions. In this example, the energy source 160 can be configured to emit energy 170 from at least two surfaces 161 of the energy source 160. For example, the energy source 160 can include a bi-directional transducer 162. However, the energy source 160 can include two separate transducers 162, which are aimed 180 degrees from each other. For example, the use of a multi-directional transducer 162 allows treatment to both an upper ROI 108' and a lower ROI 108" simultaneously. Accordingly, additional faces of the transducer 162 can facilitate treatment over a given ROI 108 in less treatment time and may use less output power.

Figure 5C:
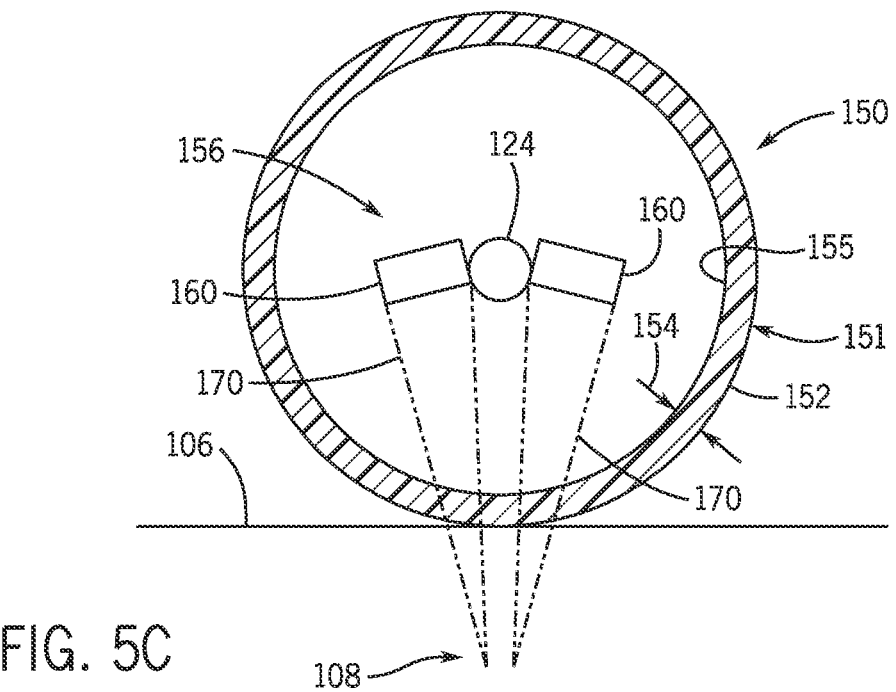
FIG. 5C provides yet another example of a cross-sectional view along the line B-B of FIG. 4, according to one aspect of the present disclosure.

FIG. 5C is a cross-sectional view, along the line B-B of FIG. 4, illustrating another example of the transducer module 150, in accordance with various configurations. As discussed herein, the axle 124 can include an energy source 160. The axle 124 can be configured to include the energy source 160 as a portion of a structure of the axle 124. As illustrated in FIG. 5C, two energy sources 160 can be coupled to the axle 124. In the example, each of the energy sources 160 is directed to separate target zones in the ROI 108. Use of multiple energy sources 160 can increase speed of treatment by increasing the amount of target zones in the ROI 108. A variety of configurations using multiple energy sources 160 can be coupled to the axle 124.

Figure 5D:
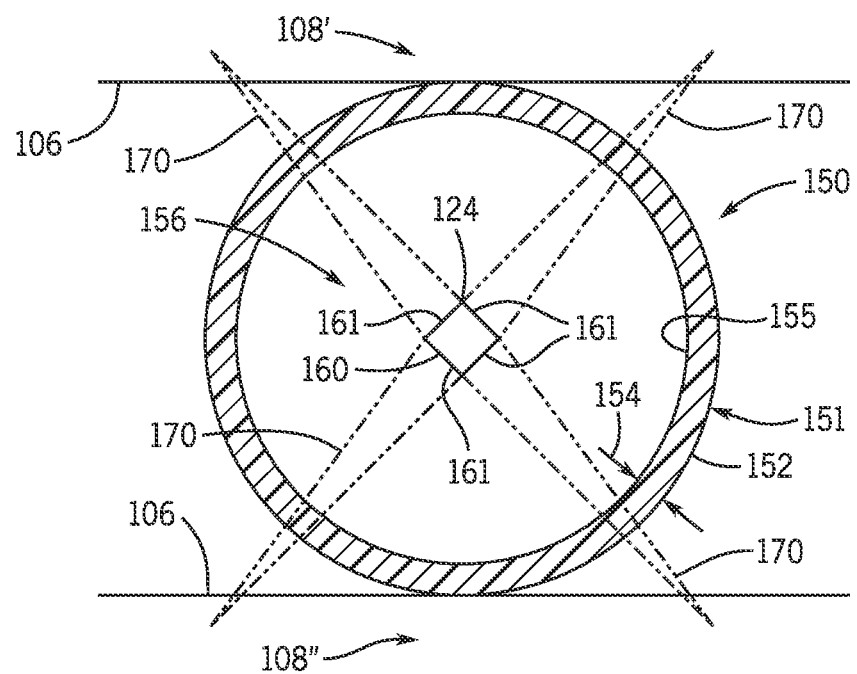
FIG. 5D provides yet another example of a cross-sectional view along the line B-B of FIG. 4, according to one aspect of the present disclosure.

FIG. 5D is a cross-sectional view, along the line B-B of FIG. 4, illustrating another example of the transducer module 150, in accordance with various configurations. As illustrated herein, the energy source 160 can be configured to emit energy 170 from at least two transmitting surfaces 161. For example, energy source 160 can be configured to emit energy from four transmitting surfaces 161. In such an example, the energy source 160 can be configured to provide treatment to both an upper ROI 108' and a lower ROI 108" in a coordinated fashion, including simultaneously or using pre-programmed delays. Thus, increasing the number of radiating surface areas can enable treatment over a larger ROI 108. Accordingly, additional faces of the energy source 160 can facilitate treatment over a given ROI 108 in less treatment time and less output power. In this example, the multidirectional energy source 160 has four different faces, however, a multidirectional energy source 160 can include a number of transmitting surfaces beyond or less than four.

Figure 6A:
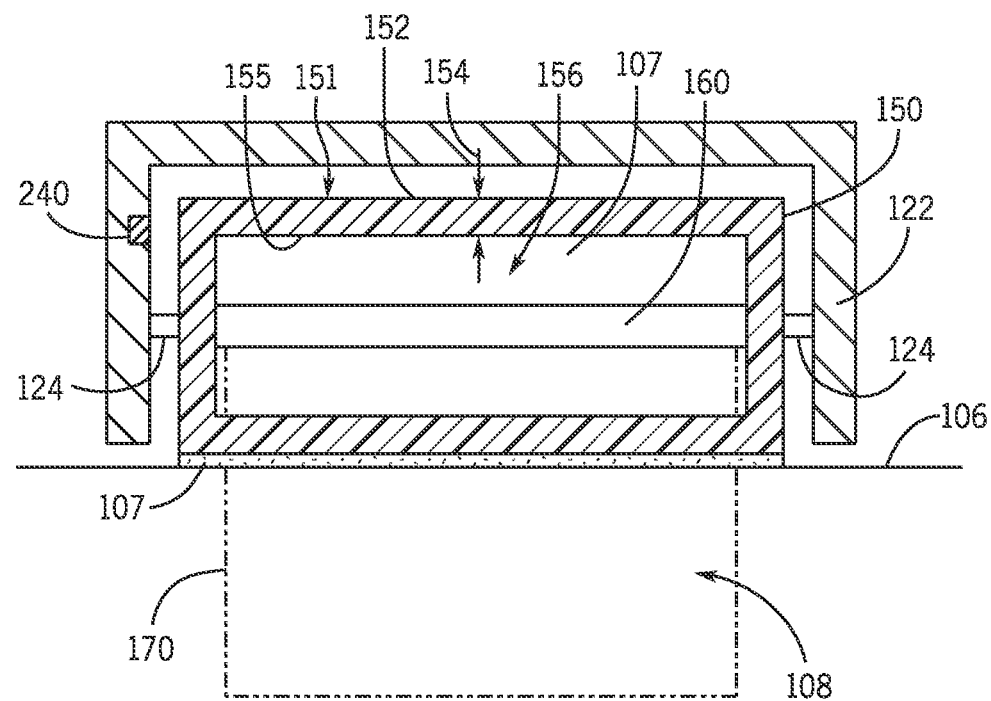
FIG. 6A provides one example of a cross-sectional view along the line A-A of FIG. 3, according to one aspect of the present disclosure.

Referring now to FIG. 6A, a cross-sectional view along the line A-A of FIG. 3 of the transducer module 150 is illustrated, in accordance with various configurations. The transducer module 150 can include a transducer module wall 151, which has an outer surface 152 and an inner surface 155. The transducer module wall 151 can have a thickness 154, which is a distance measured perpendicularly from the outer surface 152 to the inner surface 155. In various configurations, the transducer module wall 151 can be configured to provide various physical attributes to the energy 170, as further discussed herein. The transducer module 150 can be configured to have an internal volume 156, which is bordered or bounded by the inner surface 155. The internal volume 156 can be filled with a coupling medium 107, as discussed herein. An axle 124 can be located at approximately a center point of a circumference as defined by the inner surface 155. The transducer module wall 151 can rotate around the axle 124, which can be stationary relative to an external frame. Alternatively, the transducer module 150 can be stationary relative to the axle 124, and the transducer module 150 and the axle 124 can rotate relative to a stationary external frame.

The axle 124 can include an energy source 160, which optionally surrounds the structure of the axle 124. In some configurations, the energy source 160 is the axle 124. The energy source 160 can include a multi-directional transducer 162, which can include a single face or a number of faces 161. The energy source 160 can be an array of transduction elements.

Figure 6B:
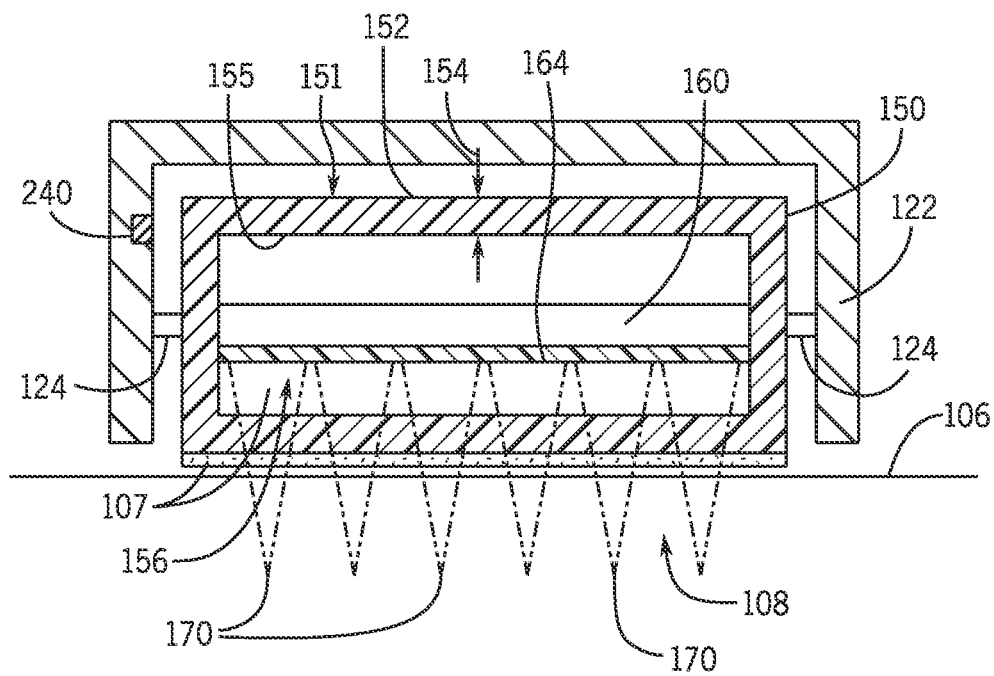
FIG. 6B provides another example of a cross-sectional view along the line A-A of FIG. 3, according to one aspect of the present disclosure.

Referring to FIG. 6B, a cross-sectional view along the line A-A of FIG. 3 of the transducer module 150 is illustrated in accordance with various configurations. In this example, the axle 124 can include the energy source 160. In some configurations the transducer module 150 can include at least one lens 164. For example, the energy source 160 can be configured with at least one lens 164 that is configured to focus the energy 170 within the ROI 108. The energy source 160 and the at least one lens 164 can be configured in a variety of ways depending on various target treatments that may include such parameters as, for example, a desired depth of energy 170, a type of focusing of energy 170, a number of lines of energy 170, and a size of the transducer module 150.

In some configurations, the lens 164 can be configured to focus the energy 170 into the ROI 108. The lens 164 can be configured to weakly focus the energy 170 into the ROI 108. The lens 164 can be configured to direct the energy 170, which is defocused, into the ROI 108. The lens 164 can be configured to direct the energy 170, which is unfocused, into the ROI 108. The lens 164 can be configured to direct the energy 170 having a planar focus into the ROI 108. Additional examples of transducer 162 and lens 164 configurations are discussed in the description of FIG. 25.

Figure 6C:
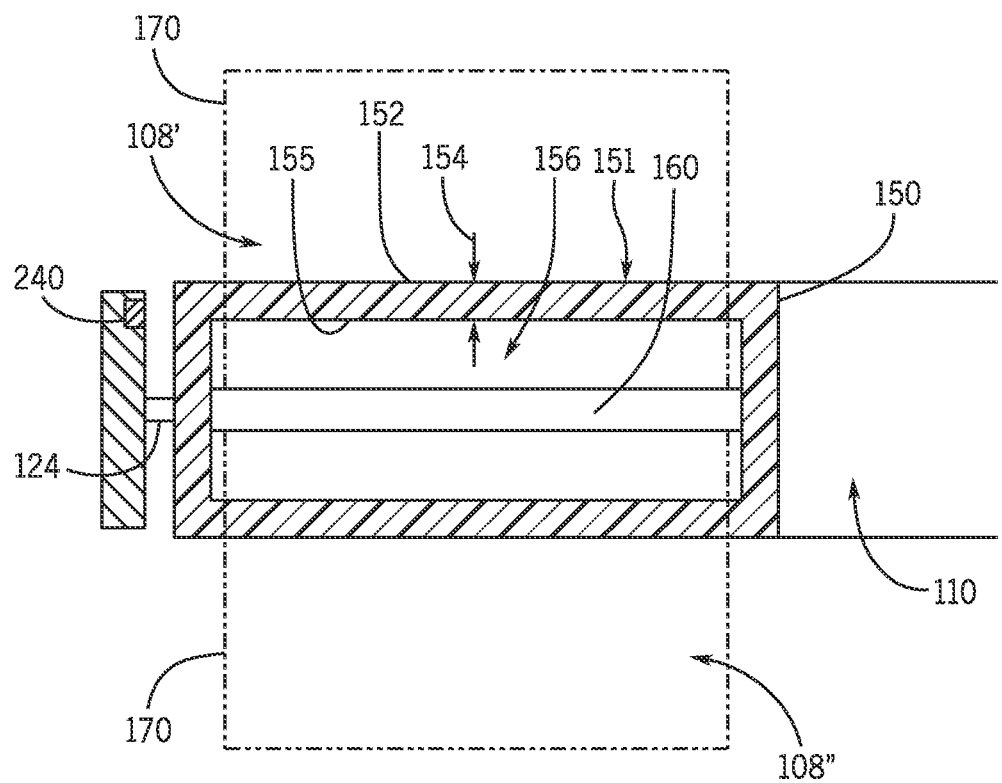
FIG. 6C provides yet another example of a cross-sectional view along the line A-A of FIG. 3, according to one aspect of the present disclosure.

FIG. 6C illustrates a cross-sectional view along the line A-A of FIG. 3 of another configuration of the transducer module 150, in accordance with various configurations. In this configuration, the transducer module 150 can rotate around the axle 124; however, the transducer module 150 can be configured for a bi-directional energy source 160. For example, the bi-directional energy source 160 illustrated in FIG. 5B can be employed in this configuration. In addition, the multi-directional energy source 160 illustrated in FIG. 5D can be employed in this configuration. In such a configuration, the energy source 160 can be configured to provide treatment to both an upper ROI 108' and a lower ROI 108" in a coordinated fashion, for example, simultaneously. Additional faces of the energy source 160 can facilitate treatment over a larger ROI 108 in less treatment time and may require less output power.

Figure 6D:
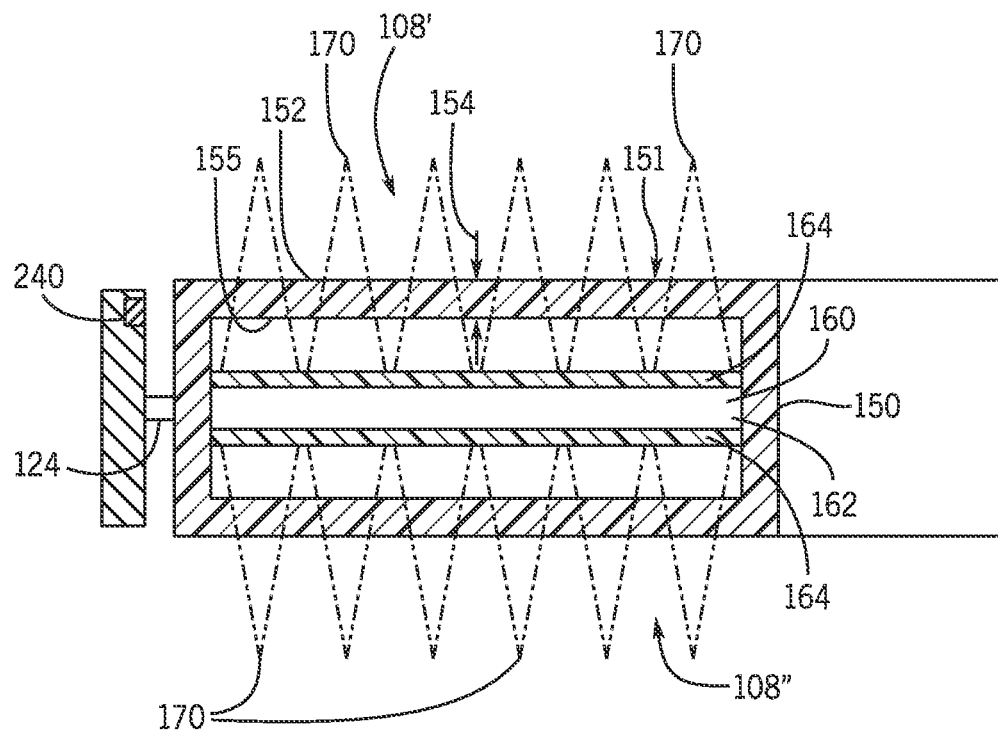
FIG. 6D provides still another example of a cross-sectional view along the line A-A of FIG. 3, according to one aspect of the present disclosure.

FIG. 6D illustrates a cross-sectional view along the line A-A of FIG. 3 of another configuration of the transducer module 150, in accordance with various configurations. In this configuration, the transducer module 150 can rotate around the axle 124. The transducer module 150 can be configured for an energy source 160 that is bi-directional or multi-directional. In this configuration, the energy source 160 can include at least one transducer 162 and at least one lens 164. For example, the at least one transducer 162 can be configured with at least one lens 164 that is configured to focus the energy 170 at a point within the ROI 108. The at least one transducer 162 and the at least one lens 164 can be configured in any number of ways depending on various target treatments which may include such parameters as for example a desired depth of energy 170, a type of focusing of energy 170, a number of lines of energy 170, and a size of the transducer module 150.

Figure 7:
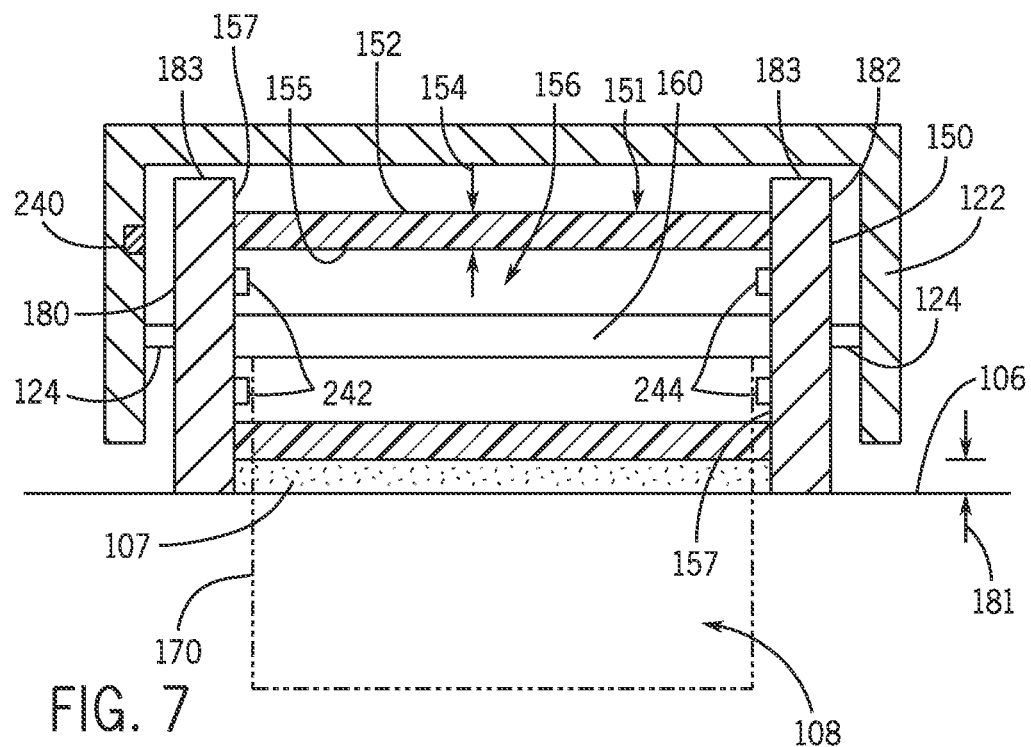
FIG. 7 illustrates a cross-sectional view along the line A-A of FIG. 3 of an alternative transducer module, according to one aspect of the present disclosure.

Now moving to FIG. 7, a cross-sectional view along the line A-A of FIG. 3 of an alternative configuration of the transducer module 150 is illustrated in accordance with various configurations. The transducer module 150 can include an end cap 157 that seals the transducer module wall 151 of transducer module 150 to form an internal volume 156. A pair of end caps 157 can seal either end of the transducer module 150. The end cap 157 can be configured to form a seal to stop liquid placed within internal volume 156 from escaping from transducer module 150. In some configurations, the end cap 157 can include a wheel 180. To help facilitate rolling of transducer module 150, the wheel 180 can have an outer surface 183 which is tacky, has a grip on the target surface 106, or otherwise increases the friction between the transducer module 150 and the target surface 105. In some examples, the wheel 180 is made of a rubber or silicon material or the like, and/or combinations thereof. The wheel 180 can include an offset 181, which is the difference between the radius of the transducer module 150 and the radius of the wheel 180.

The treatment device 100 can include a position sensor 240 in communication with the control module 110 and configured to monitor a position of the transducer module 150. The position sensor 240 or the control module 110 can calculate a speed of the rotation in the rotational direction 102 of the transducer module 150. In some configurations, the transducer module 150 includes the position sensor 240. The position sensor 240 can be integrated into the transducer module 150 or attached to the transducer module 150. The position sensor 240 can be configured to measure movement of the transducer module 150, as discussed herein.

In some configurations, the treatment device 100 can include at least a second wheel 182. To help facilitate movement of treatment device 100, the at least two wheels 180, 182 can have an outer surface 183, which has a coefficient of friction greater than zero. In other words, the wheels 180, 182 have an outer surface, which provides grip in the target surface 106. In some examples, the at least two wheels 180, 182 are made of a rubber or silicon material or the like, and/or combinations thereof. The at least two wheels 180, 182 can include an offset 181, which is the difference between the outer surface 152 of the transducer module wall and the outer surface 183 of the at least two wheels 180, 182. The offset 181 can be calibrated to hold a desired thickness of coupling medium 107 between the transducer module 150 and the target surface 106. For example, the coupling medium 107 can be water-based, light oil(s)-based, based on an emulsion of light oil and water, other coupling liquids or gels, or a combination thereof. In some applications, the coupling medium 107 can include water, light oils, or emulsions of light oil and water, which are configured to not interfere with a position sensor 240, optionally an optical position sensor 240, contained in the treatment device 100.

The offset 181 can be applicable to a configuration of the treatment device 100 containing only one wheel 180. The offset 181 can be at least 1 mm, which is measured from the target surface 106 to the outer surface 152 of the transducer module wall 151. In some configurations, the at least one wheel 180 has a circumference that is at least 2 percent greater than a circumference of a circle having an arc equal to the outer surface 152 of the transducer module wall 151. The circumference of the at least one wheel 180 can be adjusted relative to the circumference of the outer surface 152 of the transducer module wall 151 to optimize the length of the offset 181. The offset 181 can be calibrated to hold a desired thickness of coupling medium 107 between the transducer module 150 and the target surface 106.

In certain configurations, the treatment device 100 can include a temperature sensor 242. The temperature sensor 242 can be configured to sense the temperature of certain parts of the treatment device 100, such as the energy source 160 or the transducer module wall 151, a temperature of the target surface 106, a temperature of the ROI 108, or a combination thereof. The temperature sensor 242 can be located within the transducer module 150 or elsewhere in the treatment device 100.

In certain configurations, the treatment device 100 can include a contact sensor 244 for sensing coupling between the transducer module 150 or the energy source 160 and the ROI 108 or the target surface 106. The contact sensor 244 can be located within the transducer module 150 or elsewhere in the treatment device 100. In particular, both the temperature sensor 242 and the contact sensor 244 may be formed, in the illustrated non-limiting example, as rings attached to the end caps 157.

Figure 8:
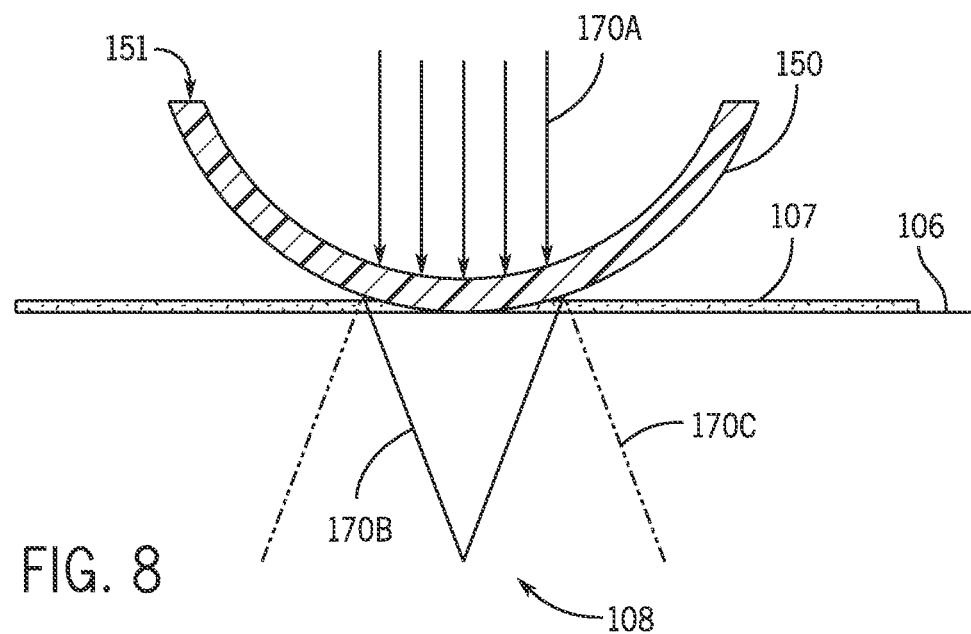
FIG. 8 is a partial view of cross section along line B-B of FIG. 4, illustrating a lensing effect, according to one aspect of the present disclosure.

FIG. 8 illustrates a lensing effect, in accordance with some configurations. The energy 170 can be focused by the transducer module wall 151. For illustration purposes, the energy 170 is collimated and is designated by energy 170A. The collimated energy 170A can be focused by a curvature of the transducer module wall 151. Accordingly, the system 100 can produce collimated energy 170A and then can focus the original energy emission thus generating energy 170B. In another example, energy 170A can be defocused by curvature of the transducer module wall 151. Accordingly, the system 100 can produce collimated energy 170A and then can defocus the original energy emission thus generating energy 170C.

Alternatively, the energy 170 can be focused by use of a phased array in the energy source 160. The energy 170 can be focused using a lens 164 in the energy source 160, as described herein. The energy 170 can be focused by a combination of a lens 164 and a phased array in the energy source 160. The energy 170 can be collimated, focused, weakly focused, unfocused, or defocused by any combination of the energy source 160, one or more lenses 164, and the transducer module wall 151.

Figure 9A:
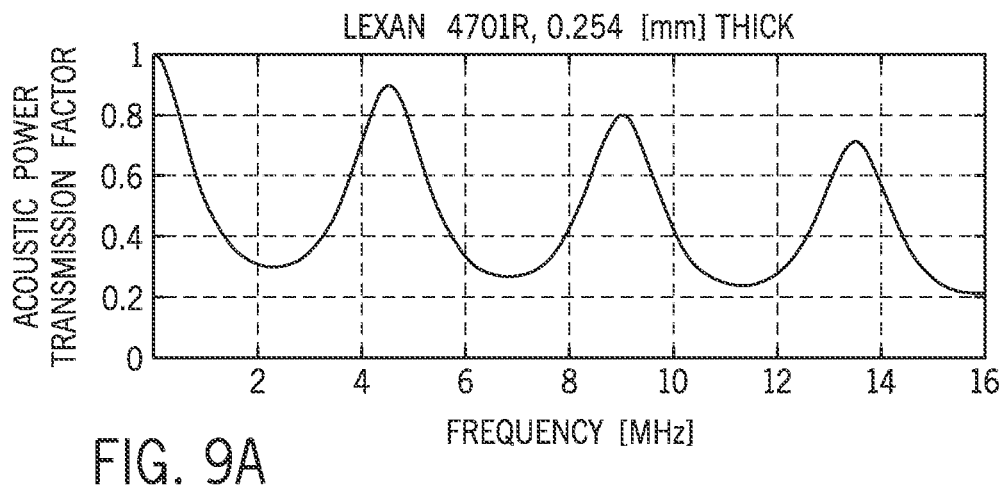
FIG. 9A is a graph of a acoustic power transmission factor versus frequency for a first transducer wall thickness.
Figure 9B:
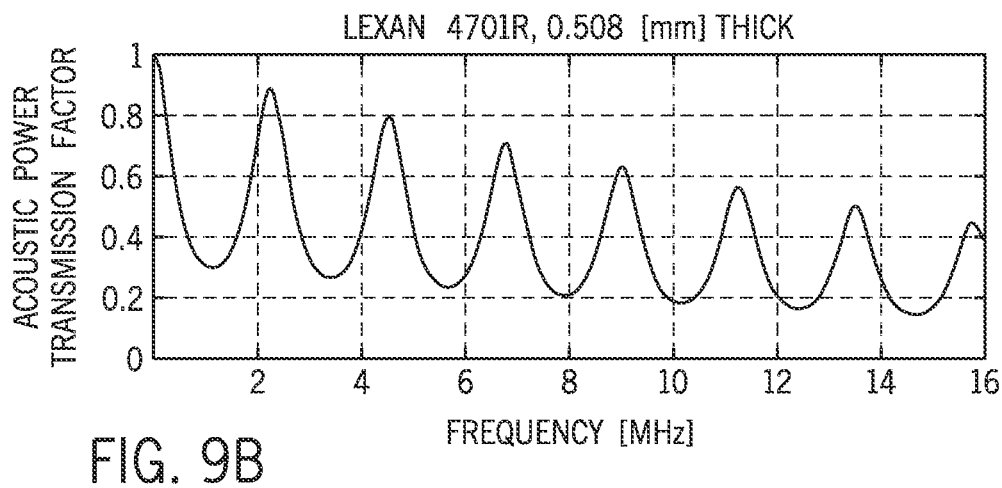
FIG. 9B is a graph of a acoustic power transmission factor versus frequency for a second transducer wall thickness.
Figure 9C:
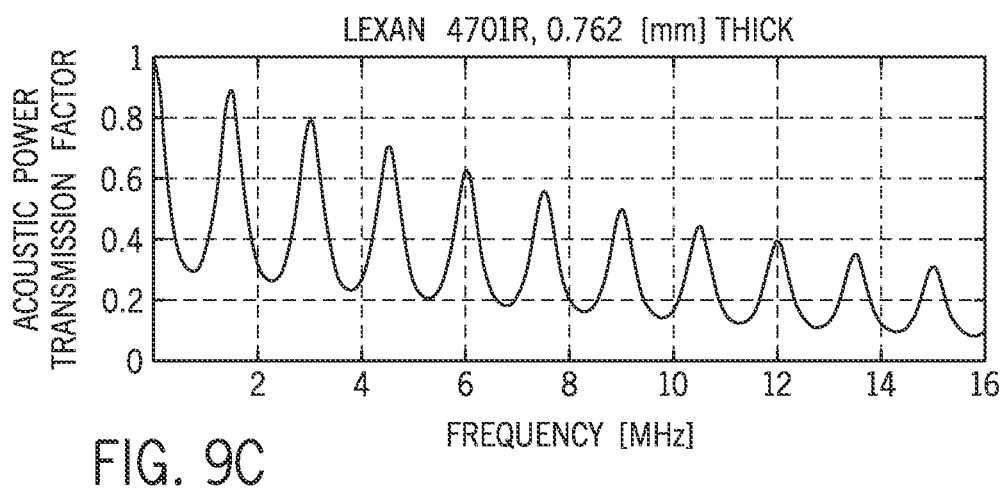
FIG. 9C is a graph of a acoustic power transmission factor versus frequency for a third transducer wall thickness.

A variety of focusing, defocusing, weakly focusing, and unfocused energy can be used to generate a desired energy field directed to the ROI 108. A combination of geometric parameters of system 100 is considered to define the desired energy field directed to the ROI 108. For example, the focusing (or defocusing or unfocused) energy 170 can depend based on: on acoustic velocity of material chosen to fill cylinder volume 156, size of beam of energy 170A emitted by energy source 160, path length between energy source 160 and inner surface 155, a lens coupled to energy source 160, and a phased array as the energy source 160. In addition, the focusing (or defocusing) of energy 170B (or 170C) can depend based on acoustic velocity of material chosen for the transducer module wall 151, thickness 154 of the transducer module wall 151, and curvature (radii) of the transducer module wall 151. The frequency of energy 170A emitted by energy source 160 should be within a narrow band width for the geometry to work and produce the desired energy (170B or 170C) directed to ROI 108. Precision of the calculated geometry can be used to achieve the desired energy (170B or 170C). If the frequency of energy 170A is outside of the narrow band width, the energy 170A reflected back to energy source 160. For example, as illustrated in FIGS. 9A through 9B, graphs are provided that show acoustic power transmission factor versus frequency plots for three different thicknesses. As demonstrated, the thickness of the outer wall will affect the bandwidth of the energy directed to the ROI. Lens geometry is based on the arc of the curvature of the outer wall.

Figure 10:
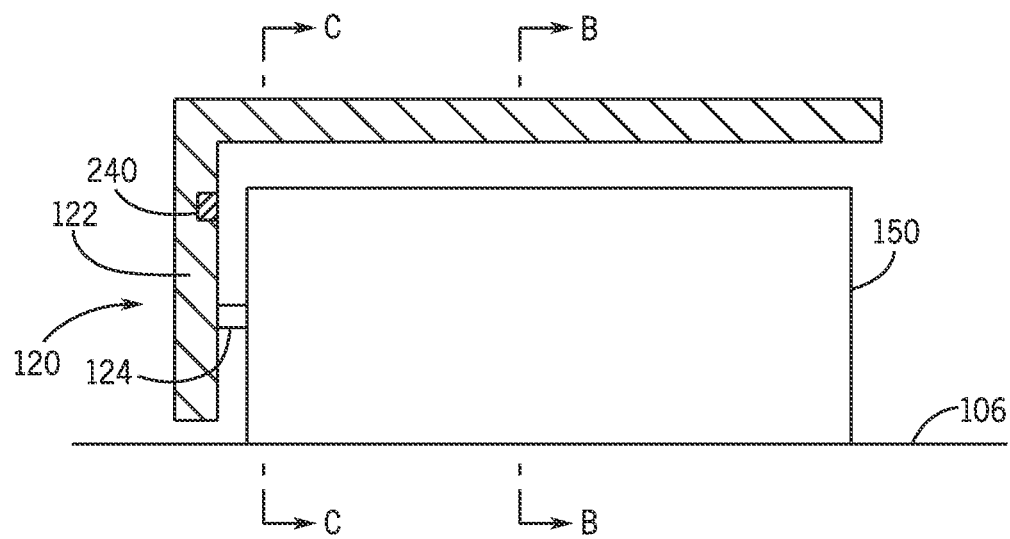
FIG. 10 is a front view illustrating an alternative configuration of a transducer module, according to one aspect of the present disclosure.

FIG. 10 illustrates a front view of an alternative configuration of the transducer module 150, which includes a single linkage 120, in accordance with various configurations. The single linkage 120 can include a strut 122, which can be configured to provide structure to the linkage 120. The single linkage 120 is coupled to the axle 124. In some configurations, the single linkage 120 can be configured for removal and attachment of the transducer module 150. In other configurations, the single linkage 120 can be configured to be permanently coupled to transducer module 150. The single linkage 120 can include a coupling configured to engage the axle 124.

The single linkage 120 can be an electronic interface between the control module 110 and the transducer module 150. For example, the strut 122 can be hollow and configured for wiring to run inside of the strut 122. In some examples, the strut 122 can be configured with a channel along a length of strut 122 for wiring to run inside of channel in the strut 122. The strut 122 can include a thin film electrode configured to provide an electronic interface between the control module 110 and the transducer module 150. In some configurations, the strut 122 can include a position sensor 240.

Figure 11:
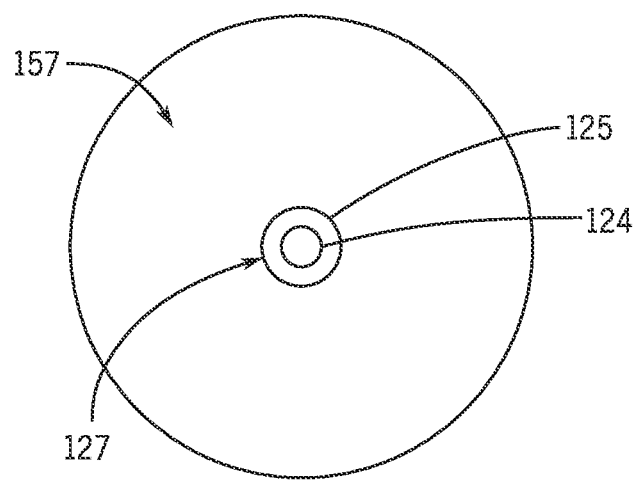
FIG. 11 is a cross-sectional view along the line C-C of FIG. 4, according to one aspect of the present disclosure.

With reference to FIG. 11, a cross-section of the transducer module 150 along the line C-C of FIG. 4 or FIG. 10 is illustrated, in accordance with various configurations. This view of the transducer module 150 illustrates an end cap 157 that surrounds the axle 124. A seal 125 can be configured around the axle 124 to seal between the axle 124 and the end cap 157. In some configurations, the end cap 157 can rotate relative to the axle 124, so the seal 125 may include an anti-friction mechanism. In some configurations, the anti-friction mechanism can lower a coefficient of friction between the seal 125 and the axle 124. In some configurations, the anti-friction mechanism can lower a coefficient of friction between the seal 125 and the end cap 157. In some configurations, the anti-friction mechanism can lower a coefficient of friction between the axle 124 and the linkage 120. The anti-friction mechanism can include a variety of configurations, including a mechanical device, lubricant, film, elastomeric composition, or combination thereof, which lowers a coefficient of friction between two bodies. For example, the anti-friction mechanism can include at least one ball bearing. In some examples, the anti-friction mechanism can include at least one roller bearing. The anti-friction mechanism can include a lubricant. The anti-friction mechanism can include a film which is configured to reduce friction. The anti-friction mechanism can include an elastomeric composition configured to reduce friction. In certain configurations, the axle 124 can be coupled to the linkage 120 with a scotch yoke 127.

A coupling of the linkage 120 to the axle 124 can be configured to allow the transducer module 150 to rotate while prevent binding, twisting and/or breaking of the wiring of the linkage 120 during rotation of the transducer module 150. The wiring can be configured to provide power from the control module 110 to the energy source 160. The wiring can be configured to control the energy source 160 with the control module 110. In some configurations, a power supply can be configured to power energy source can be located in the transducer module 150. For example, a battery (disposable or rechargeable) can be coupled to the energy source 160 and can be configured to power the energy source 160. In one configuration, the axle 124 can include a magnet and a wire coil around the magnet, which is configured to generate electricity and is coupled to a rechargeable battery.

Figure 12:
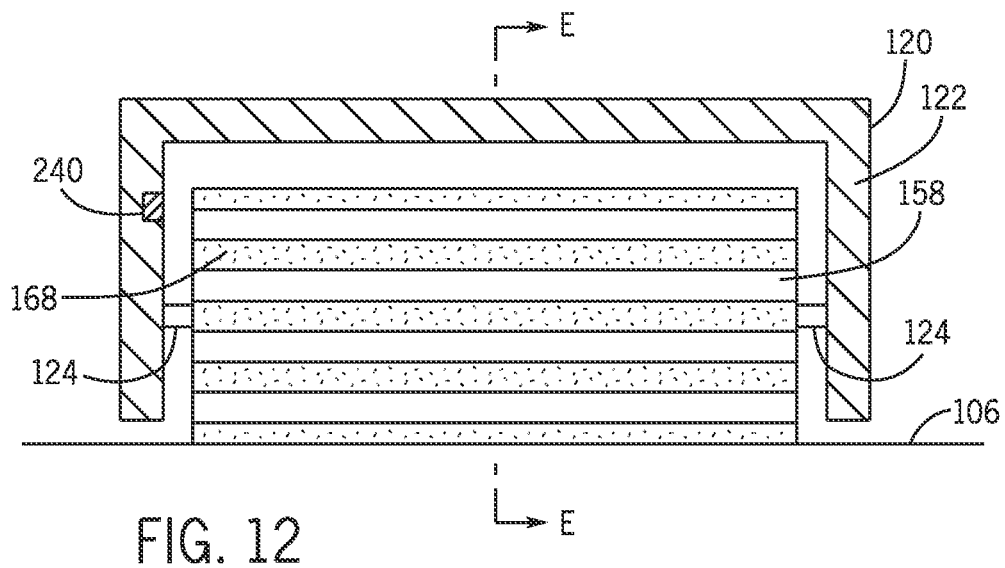
FIG. 12 is a front view illustrating a multi-surface configuration of a transducer module, according to one aspect of the present disclosure.
Figure 13:
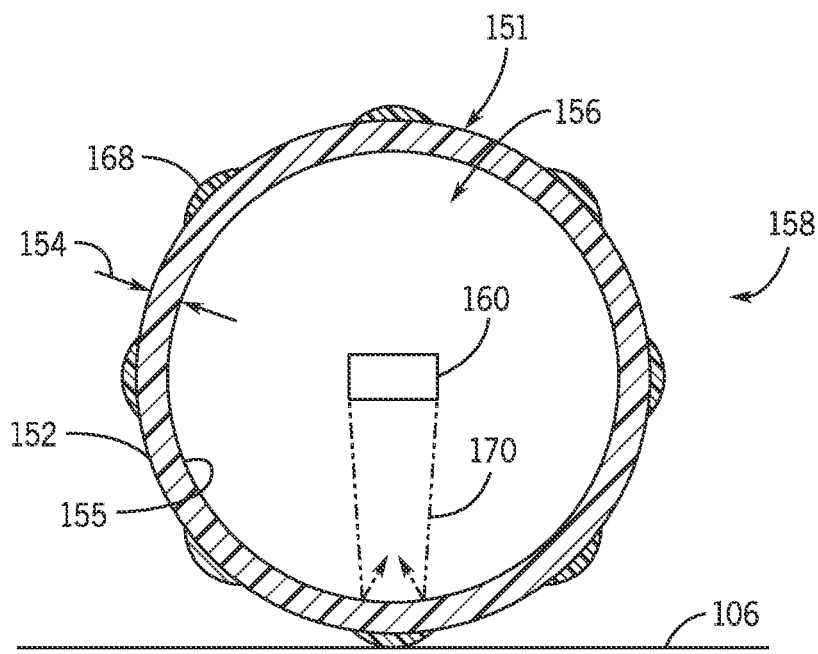
FIG. 13 is a first cross-sectional view along the line E-E of FIG. 12, according to one aspect of the present disclosure.
Figure 14:
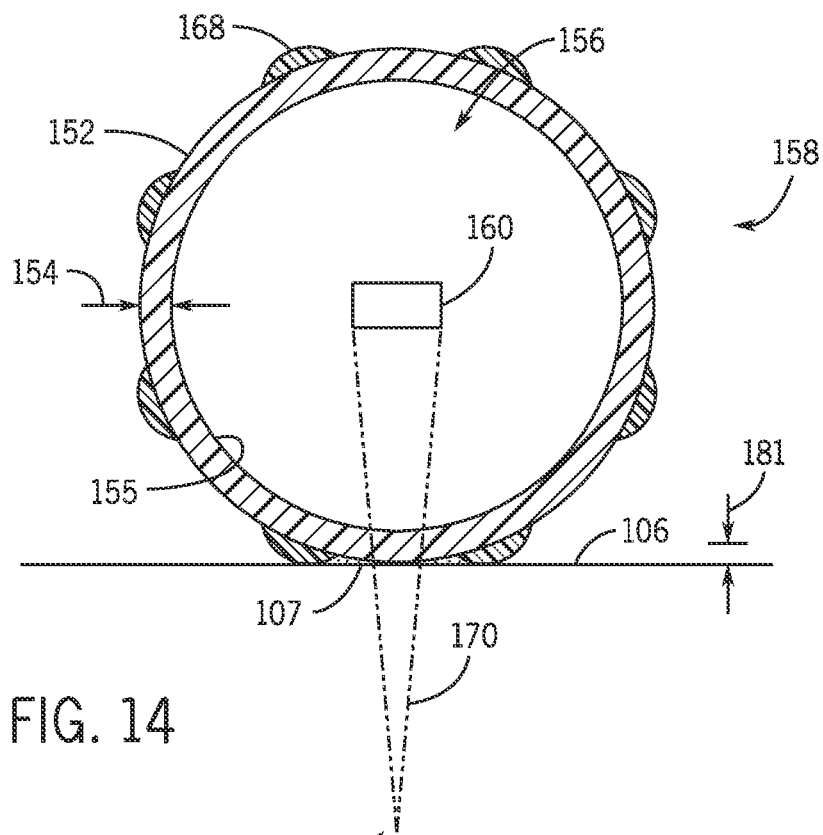
FIG. 14 is a second cross-sectional view along the line E-E of FIG. 12, according to one aspect of the present disclosure.

FIGS. 12-14 illustrate a variation of the transducer module 150, which include a multi-surface transducer module 158, in accordance with various configurations. The multi-surface transducer module 158 can be equivalent to the transducer module 150, as described herein. The multi-surface transducer module 158 can include a transducer module wall 151 having an outer surface 152 and an inner surface 155. The transducer assembly body 158 can include a transducer module wall 151 having a thickness 154, which is a distance measured perpendicularly from the outer surface 152 to the inner surface 155. In various configurations, the thickness 154 can be configured to provide various physical attributes to the energy 170, as further discussed herein. The multi-surface transducer module 158 can be configured to have an internal volume 156, which is bordered or bounded by the inner surface 155. The internal volume 156 can be filled with a coupling medium 107, as discussed herein. An axle 24 can be located at approximately a center point of a circumference as defined by the inner surface 155. The transducer assembly body 158 can rotate around the axle 124 which can be stationary relative to an external frame. Alternatively, the transducer module 158 can be stationary relative to the axle 124, and the transducer module 158 and the axle 124 can rotate relative to a stationary external frame. The axle 124 can include an energy source 160, as described herein.

A plurality of parallel friction strips 168 can be affixed to the outer surface 152 of the transducer module wall 151 of the multi-surface transducer module 158. The friction strips 168 can provide friction to roll the multi-surface transducer module 158 along the target surface 106. In some configurations, as illustrated in FIG. 13, the friction strips 168 do not allow the energy 170 to pass through. In certain configurations, the friction strips 168 reflect the energy 170. In such configurations, the energy 170 can be "pulsed" in to the ROI 108 by blocking the energy 170 when the friction strip 168 contacts the surface and allowing the energy 170 into the ROI 108 when the outer surface 152 of transducer module wall 151 of the multi-surface transducer module 158 is coupled to the target surface 106, as illustrated in FIG. 14. However, the friction strips can be transparent to the energy 170. The energy source 160 can be turned on or off to synchronize to an angle of rotation to emit energy 170 either when clear of the friction strip 168, blocked by the friction strip 168, or both.

In some configurations, the multi-surface transducer module 158 the can include an offset 181, which is the difference between the outer surface 152 of the transducer module wall 151 at a point nearest to the surface 106 and the contact points of friction strips 168 with the surface 106. The offset 181 can be calibrated to hold a desired thickness of coupling medium 107 between the multi-surface transducer module 158 and the target surface 106, as illustrated by FIG. 14. The offset 181 can be calibrated to hold the coupling medium between the friction strips 168. In some configurations, a plurality of friction strips 168 can hold coupling medium 107 on the assembly 158 between the friction strips 168.

Figure 15:
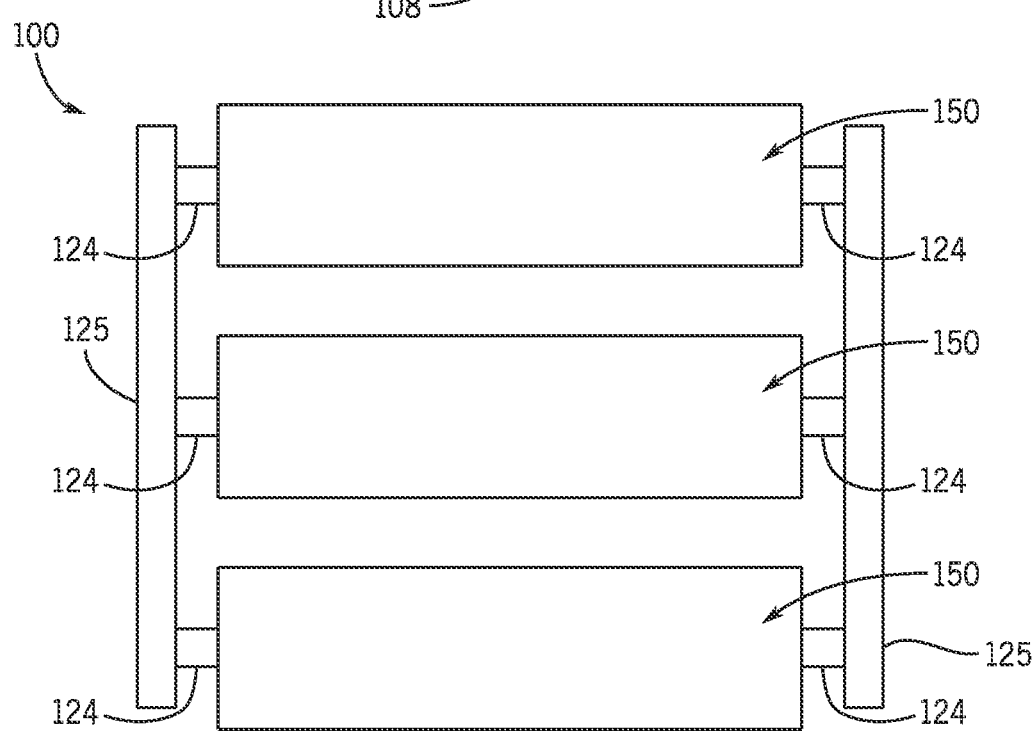
FIG. 15 is a top view illustrating an exemplary treatment system including a plurality of transducer modules, according to one aspect of the present disclosure.

FIG. 15 illustrates a configuration of the treatment device 100 including a plurality of transducer modules 150, which are coupled together with a floating axle 125. Such a configuration can be used to treat a larger surface area for example, for treating fat and/or cellulite. In addition, such a configuration can be used on uneven or curved surfaces.

In some configurations, the axles 124 can be moveable. The axles 124 can be configured to be sensitive to mechanical pressure on any of the transducer modules 150. At least one of the axles 124 can move up into the floating axle 125 in response to an increase in mechanical pressure on any of the transducer modules 150. In the opposite, at least one of the axles 124 can move down towards target surface 106 in response to a decrease in mechanical pressure on any of the transducer modules 150. For example, the axles 124 can be biased, for example, spring-loaded, to move up and down along the floating axle 125 to compensate for changes in the target surface 106 above the ROI 108. In some configurations, the axles 124 can move along a z-axis in relation to the target surface 106.

Figure 16:
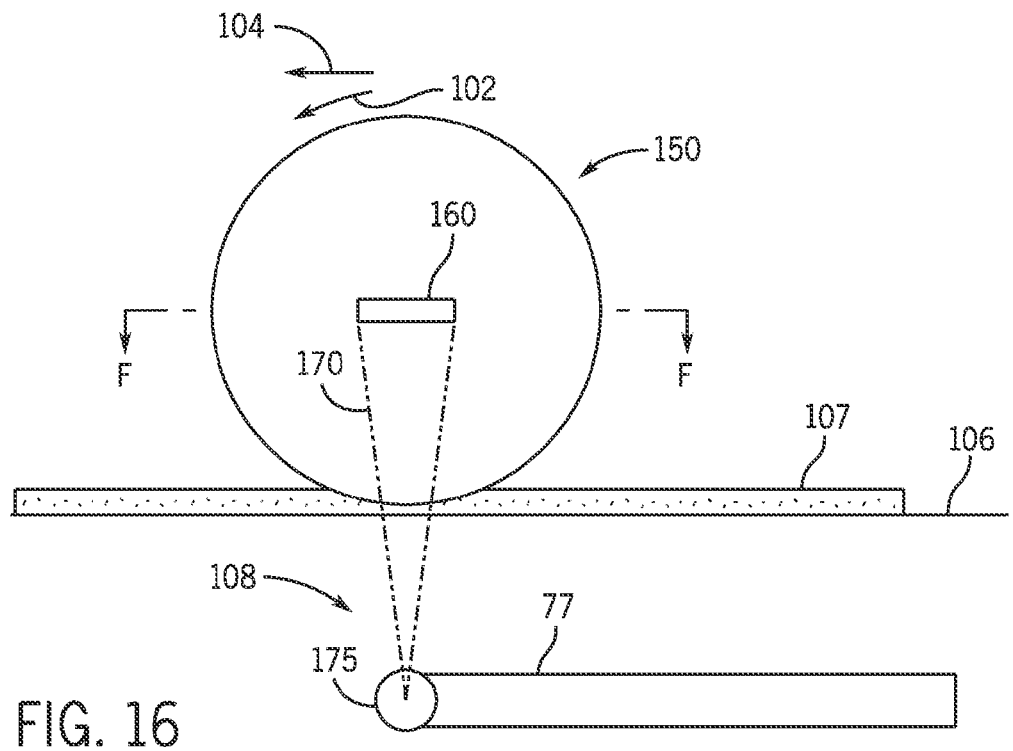
FIG. 16 is a side view of a transducer module illustrating methods of treatment, according to one aspect of the present disclosure.
Figure 17:
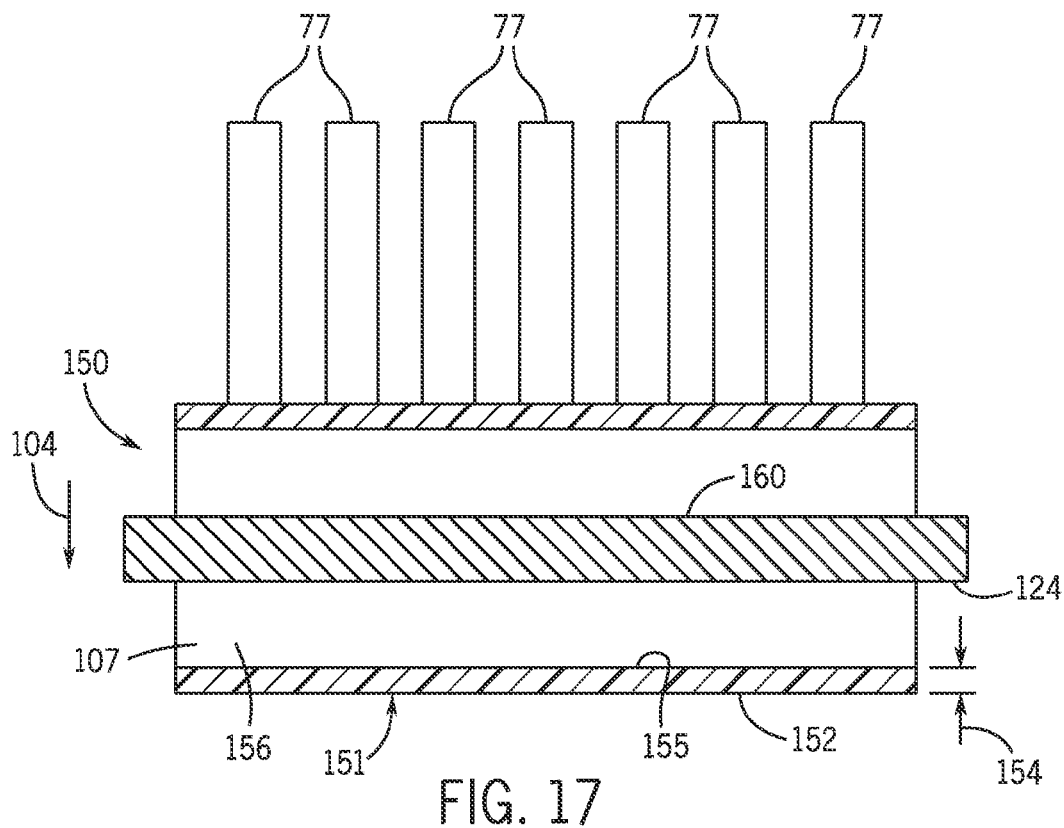
FIG. 17 is a cross-sectional view along the line F-F of FIG. 16, according to one aspect of the present disclosure.

Referring to FIGS. 16 and 17, some examples of methods for performing treatment using the above-described systems can be described. The transducer module 150 can provide energy 170 into the ROI 108 and create an elevated thermal region 175. As the transducer module 150 is rotated in the rotational direction 102 and moved in the forward direction 104, the elevated thermal region 175 creates treated region 77. As illustrated, the treated region 77 may be formed as a set of lines, which are produced using energy 170 from the energy source 160. To this end, the energy 170 from the energy source 160 may delivered in a continuous fashion. Additionally or alternatively, the energy 170 may be pulsed, such that the treated region 77 can is formed as an array of treatment zones. The treated region 77 can be a region of thermal injury in subcutaneous tissue.

As treatment continues, the system 100 can move in a forward direction 104, which can rotate in the rotational direction 102 the transducer assembly 150 along the surface 106 and treat a larger ROI 108. However, the system 100 can move in a motion that is opposite the forward motion 104, which will rotate opposite to the rotational direction 102. Furthermore, the system 100 can be moved back and forth in any pattern that the user chooses. The coupling medium 107 can be applied to the target surface 106 during rotation 102 of the transducer assembly 150. The coupling medium 107 can be any such materials, gels, medicaments, as discussed herein, or are known to those skilled in the art now or at any time in the future.

In various configurations, the transducer module 150 can be configured to have an internal volume 156 that is bordered or bounded by the inner surface 155 of the transducer module wall 151. The internal volume 156 can be filled with a coupling medium 107. The transducer module 150 can further include a transducer module wall 151 including a material having a thickness 154 which may be transparent or substantially transparent to ultrasound energy. In some configurations, the transducer module 150 can include a transducer 162. In some configurations, the transducer module 150 may include an acoustic matching layer. The transducer module 150 can include a path length, which is a distance from the transducer 162 to the inner surface 155. The transducer module 150 has a thickness 154, which is a distance measured perpendicularly from the outer surface 152 to the inner surface 155.

In some configurations, the energy 170 may be delivered as a continuous wave emission. The transducer module 150 can couple the transducer 162 to ROI 108 and facilitates the transfer of the energy 170 from transducer 162 through the coupling medium 107 that is present and the transducer module wall 151 and into ROI 108. However, if the transducer module 150 is uncoupled from ROI 108 and is coupled to air, the transducer module wall can become a reflector and reflect all or at least a majority of the energy 170 back to transducer 162 as reflected energy.

Figure 18:
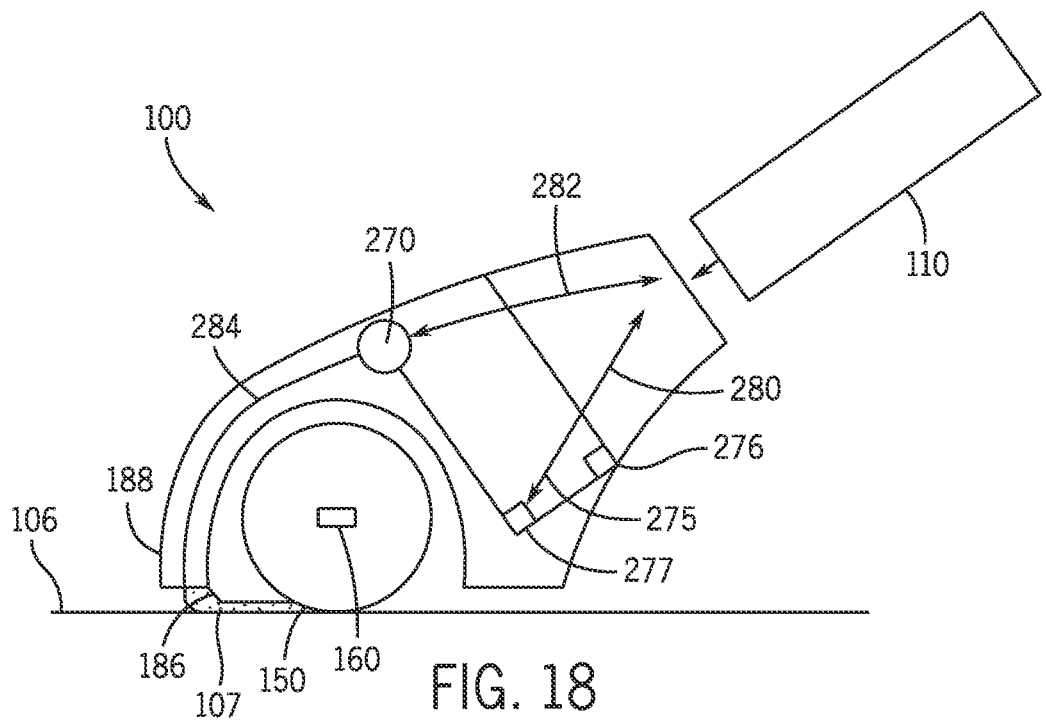
FIG. 18 is a cross-sectional view of FIG. 2 illustrating an exemplary treatment device including an acoustic coupling medium applicator, according to one aspect of the present disclosure.

Moving to FIG. 18, an example of the treatment device 100 is illustrated as a cross-sectional view of, for example, the system of FIG. 2. As discussed herein, the treatment device 100 can include a control module 110, a coupling medium application device 105, and a transducer module 150. In some configurations, the coupling medium application device 105 can include a coupling medium reservoir 275 that is in communication with a pump 270, an application tube 284, and a nozzle 188. In addition, the coupling medium application device 105 can include a fill port 276 and level sensor 277. As the treatment device 100 moves, the movement of the transducer module 150 is communicated to the control module 110, as discussed herein. The pump 270 is configured for communication 282 with the control module 110. As the movement of the transducer module 150 is received by the control module 110, calculations are made within the control module 110 and are sent via communication 282 to instruct the pump 272 to meter out a desired amount of coupling medium 107 from the coupling medium reservoir 277 into the application tube 284. The desired amount of coupling medium 107 moves through the application tube 284 through the nozzle 188 and onto the target surface 106 to provide coupling between the transducer module 150 and the ROI 108. The nozzle 188 can include a sweep 186 configured to apply an even coat of the coupling medium 107 onto the surface 106.

In some applications, the nozzle 188 can include a valve configured to open for application of the coupling medium 107 onto the target surface 106 or to close when the transducer module 150 has stopped. The level sensor 277 can be configured for communication 280 with the control module 110. In some applications, the level sensor 277 provides communication 282 to control module 110, which indicates a level of coupling medium 107 remaining in the reservoir tank 275 and, for example, when the reservoir tank 275 is empty. Upon receiving an empty communication, the control module 110 can stop operation of transducer device 100. In some aspects, upon receiving level communications indicating empty or near empty conditions, the control module 110 can communicate to user a warning signal such as a visual indicator and/or an audio signal. The coupling medium reservoir 275 can be refilled via the fill port 276.

The coupling medium 107 can be any such materials, gels, medicaments, as discussed herein, or are known to those skilled in the art now or at any time in the future. In some configurations, the coupling medium application device 105 includes a bias member, which is employed to push the coupling medium 107 onto transducer assembly 150 and/or keep the coupling medium 107 in connect with the transducer assembly 150. The coupling medium application device 105 can be adapted to be employed with any of the configurations illustrated in FIG. 6 A-D. In addition, the coupling medium application device 105 can be adapted to any of the configurations of the transducer module 150, including the configuration illustrated as transducer module 151.

The transducer module 150 can include a transducer module wall 151 having an outer surface 152 and an inner surface 155. The transducer module wall 151 can have a thickness 154 which is distance measured perpendicularly from the outer surface 152 to the inner surface 155. In various configurations, the thickness 154 can be configured to provide various physical attributes to ultrasound energy 170, as further discussed herein. The transducer module 250 can be configured to have an internal volume 156 which is bordered or bounded by the inner surface 155. The internal volume 156 can be filled with a coupling medium 107, as discussed herein.

The transducer module 150 include an energy source 160, such as an ultrasound transducer, configured to transmit acoustic energy 170 into a region of interest 108 at and/or below a surface 106. The transducer module 250 can include an arced outer annular wall 151 having a thickness 154 of about one-half wavelength of the acoustic energy 170 and configured to encase the energy source 160 and a coupling solution 156. The treatment module 250 can include a coupling sensing system in communication with the control module 110 and configured with a prescribed distance between the source 160 and an inner surface of the transducer module 150 to determine whether the energy source 160 is coupled to the ROI 108 using an interaction of the acoustic energy 170 with the thickness 154 of about one-half wavelength. The coupling sensing system can be configured to determine whether the energy source 160 is coupled to the ROI 108 by monitoring an amount of reflection of the acoustic energy 170 back to the transducer 162 by the outer surface 151 having the thickness 154 of one-half wavelength of the acoustic energy.

In some aspects, a bottom portion of the transducer module 150 can be configured with a curved outer surface 151 which has the thickness 154 of about one-half wavelength, which is an acoustic window. In such aspects, the remainder of the transducer module 250, with the acoustic window subtracted, can be made of a material that does not or only partially transmissive to acoustic energy and/or has a thickness 154 greater than one-half wavelength.

Figure 19:
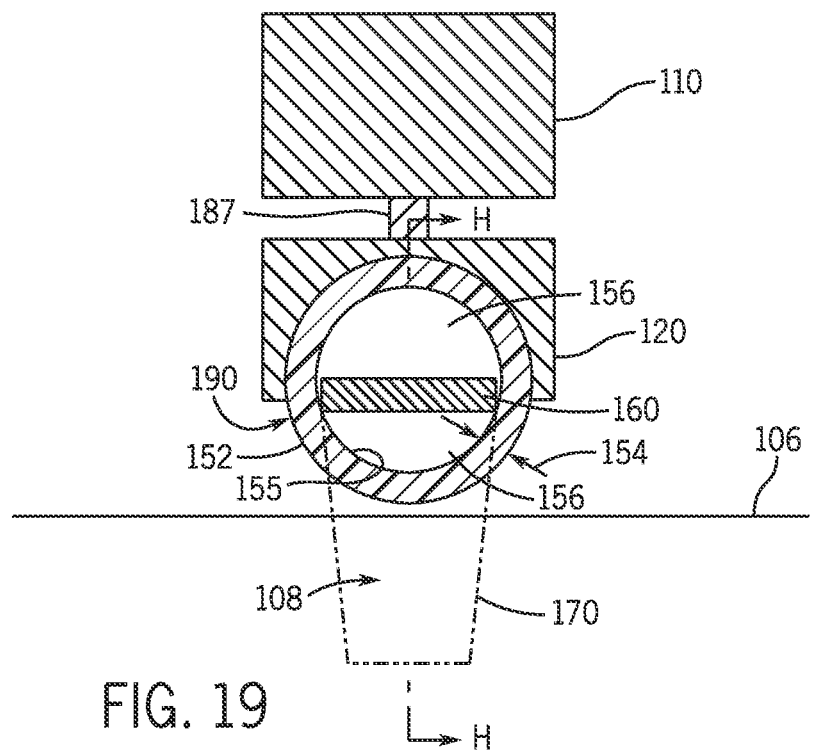
FIG. 19 illustrates an exemplary transducer module including a spherical transducer assembly, according to one aspect of the present disclosure.

FIG. 19 illustrates a spherical transducer roller 190, in accordance to various non-limiting configurations. The spherical transducer roller 190 can be useful for treating small areas. The spherical transducer roller 190 can be employed in surgical procedures, such as, for example, for minimally invasive procedures, such as, laparoscopy.

Some configurations provide a system 100, which includes an alternative configuration of the spherical transducer roller 190. The system 100 can include a control module 110 and a spherical transducer roller 190. An axle 124 can couple the transducer module 150 to the control module 110. The axle 124 can provide an electronic interface between spherical transducer roller 190 and the control module 110. At least one linkage 120 can couple the spherical transducer roller 190 to the control module 110. The linkage 120 can provide an electronic interface between spherical transducer roller 190 and the control module 110. The spherical transducer roller 190 can be configured to contact a target surface 106. The linkage 120 is coupled to pivot 187, which provides a second axis of rotation for the spherical transducer roller 190.

The spherical transducer roller 190 can include a transducer module wall such as illustrated and described above, which has an outer surface 152 and an inner surface 155. The transducer module wall has a thickness 154, which is distance measured perpendicularly from the outer surface 152 to the inner surface 155. In various configurations, the thickness 154 can be configured to provide various physical attributes to ultrasound energy 170, as further discussed herein. The transducer module wall can be configured to have an internal volume 156 which is bordered or bounded by inner surface 155. The internal volume 156 can be filled with a coupling medium 107, as discussed herein. At approximately a center point of a circumference as defined by inner surface 155 is the location of the axle 124. The transducer module wall can rotate around the axle 124, which is stationary. The axle 124 can include an energy source 160, coupled to the axle 124. In some configurations, the energy source 160 is the axle 124. For example, along the line H-H, the energy source 160 can be any of the configurations discussed in the description of FIG. 5A-D. The energy source 160 can be an array of transduction elements. The energy source 160 can include a transducer 162, which is cut or diced to create a plurality of transducer elements in the transducer 162. The cut or diced portion of the transducer 162 can create an array of transducer elements, which can be directed from various points a spherical transducer 162. In some configurations, the plurality of transducer elements can be powered individually and in some configurations the plurality of transducer elements can be controlled individually. Accordingly, the energy 170 directed to the ROI 108 is the same; no manner the position of the system 100.

In some configurations, the axle 124 can include the energy source 160. In some configurations, the energy source can include at least one transducer 162 and at least one lens 164. For example, the at least one transducer 162 can be configured with at least one lens 164, which is configured to focus the energy 170 at a point within subcutaneous tissue 108. At least one transducer 162 and the at least one lens 164 can be configured in any number of ways depending on various target treatments, which may include such parameters as for example desired depth of energy 170, type of focusing of energy 170, number of lines of energy 170, and size of spherical transducer roller 190.

A coupling of the linkage 120 to the axle 124 can be configured to allow the spherical transducer roller 190 to rotate while prevent binding, twisting and/or breaking of the wiring of the linkage 120 during rotation of the spherical transducer roller 190. The wiring can be configured to provide power from control module 110 to energy source 160. The wiring can be configured to control energy source 160 with the control module 110. In some configurations, a power supply can be configured to power energy source can be located in the spherical transducer roller 190. For example, battery (disposable or recharge able) can be coupled to energy source 160 and can be configured to power energy source 160. In one configuration, the axle 124 includes a magnetic and a wire coil around the magnet, which is configured to generate electricity and is coupled to a rechargeable battery.

Figure 20:
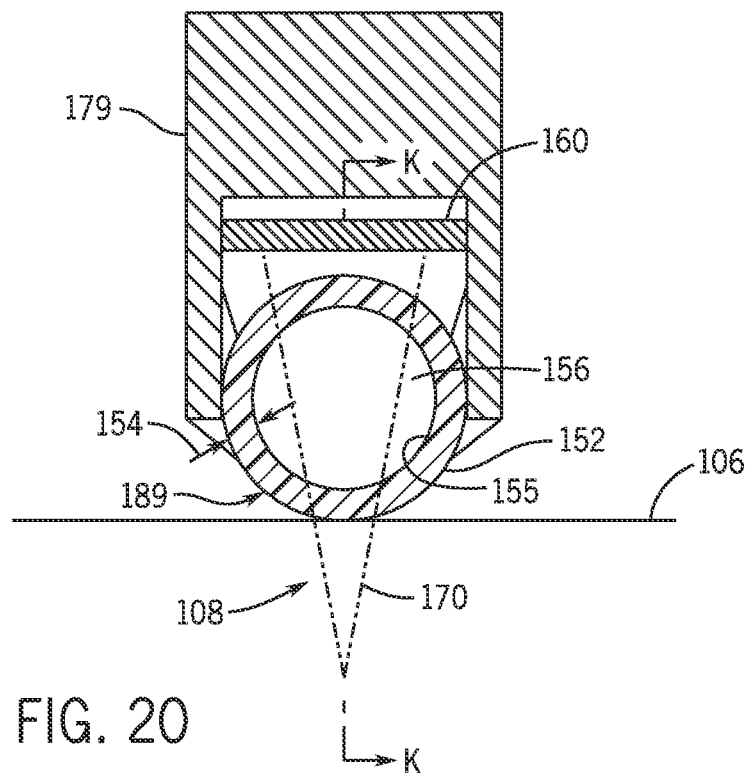
FIG. 20 illustrates exemplary transducer module including a roller ball assembly, according to one aspect of the present disclosure.
Figure 21:
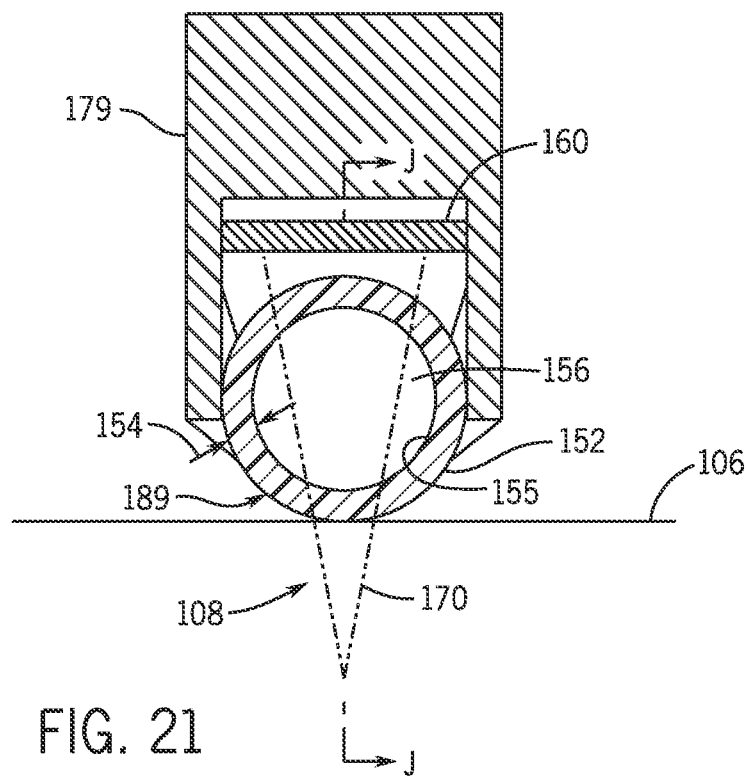
FIG. 21 illustrates the transducer module described above including a roller ball assembly, according to one aspect of the present disclosure.

With reference to FIGS. 20 and 21, a roller ball module 179 is illustrated, in two cross-sectional views. FIG. 20 is a cross-sectional view along the line J-J of FIG. 21. FIG. 21 is a cross-sectional view along the line K-K of FIG. 20. The roller ball module 179 can include a roller ball body 189, which has an outer surface 152 and an inner surface 155. The roller ball body 189 has a thickness 154, which is a distance measured perpendicularly from the outer surface 152 to the inner surface 155. In various configurations, the thickness 154 can be configured to provide various physical attributes to ultrasound energy 170, as further discussed herein. The roller ball body 189 can be configured to have an internal volume 156 which is bordered or bounded by the inner surface 155. The internal volume 156 can be filled with a coupling medium 107, as discussed herein.

In a manners similar to that described above, the roller ball module 179 can include a coupling sensing system in communication with the control module 110 and configured with a prescribed distance between the source 160 and an inner surface of the transducer module 250 to determine whether the energy source 160 is coupled to the ROI 108 using an interaction of the acoustic energy 170 with the thickness 154 of about one-half wavelength. The coupling sensing system can be configured to determine whether the energy source 160 is coupled to the ROI 108 by monitoring an amount of reflection of the acoustic energy 170 back to the transducer 162 by the outer surface 152 of the module wall, which has the thickness 154 of about one-half wavelength of the acoustic energy.

In certain configurations, the treatment device 100 can be configured as a hand-held device. In one configuration, a treatment device 100 can include a transducer module 150, a position sensor 240, a tissue contact sensor, a control module 110, and a communication interface linking the transducer module 150, the sensors and the control module 110. In one configuration, a treatment device 100 can include a position sensor 240, a control module 110, a rechargeable power supply, and a transducer module 150, which include at least one ultrasound transducer 160. In accordance with one configuration, a treatment device 100 can include a position sensor 240, a control module 110, an acoustic coupling medium dispenser 105, and a transducer module 150, which includes at least one ultrasound transducer 160. In certain configurations, the target surface 106 can be a skin surface, a subcutaneous surface, a mucosal surface, an internal organ surface, or a combination thereof.

In some configurations, the control module 110 can be capable of coordination and control of the treatment process to achieve the desired therapeutic effect on ROI 108. For example, in some configurations, the control module 110 may include power source components, sensing and monitoring components, one or more RF driver circuits, cooling and coupling controls, and/or processing and control logic components.

The control module 110 may be configured in a variety of ways to implement treatment device 100 for controlled targeting of a portion of ROI 108. For example, for power sourcing components, the control module 110 may form one or more direct current (DC) power supplies capable of providing electrical energy for the entire control module 110, including power required by a transducer electronic amplifier/driver. A DC current sense or voltage sense device may also be provided to confirm the level of power entering amplifiers/drivers for safety and monitoring purposes.

In some configurations, amplifiers/drivers may include multi-channel or single channel power amplifiers and/or drivers. In some configurations for transducer array configurations, amplifiers/drivers may also be configured with a beam former to facilitate array focusing. An exemplary beam former may be electrically excited by an oscillator/digitally controlled waveform synthesizer with related switching logic.

Power sourcing components may also include various filtering configurations. For example, switchable harmonic filters and/or matching may be used at the output of amplifier/driver to increase the drive efficiency and effectiveness. Power detection components may also be included to confirm appropriate operation and calibration. For example, electric power and other energy detection components may be used to monitor the amount of power entering transducer module 150.

Additionally, an exemplary control module 110 may further include a system processor and various digital control logic, such as one or more of microcontrollers, microprocessors, field-programmable gate arrays, computer boards, and associated components, including firmware and control software, which may be capable of interfacing with user controls and interfacing circuits as well as input/output circuits and systems for communications, displays, interfacing, storage, documentation, and other useful functions. System software may be capable of controlling all initialization, timing, level setting, monitoring, safety settings, and other system functions desired to accomplish user-defined treatment objectives. Further, various control switches, touch panels, multi-touch panels, capacitive and inductive switches, may also be suitably configured to control operation.

The control module 110 can be configured to communicate with a wireless device via wireless interface. Typically, the wireless device has a display and a user interface such as, for example, a touch screen or keyboard. Examples of a wireless or mobile device can include, but are not limited to, cell phones, a smart phones, computers, laptops, netbooks, tablets, or any other such device now known or developed in the future. Accordingly, the treatment device 100 can include any hardware, such as, for example, electronics, antenna, and the like, as well as, any software that may be used to communicate via wireless interface.

In certain configurations, the control module 110 can be a portable device. For example, the control module 110 can include a cell phones, a smart phones, computers, laptops, netbooks, tablets, or any other such device now known or developed in the future. The functions of the control module 110 can be programmed in the portable device. For example, the control module 110 functions can be downloaded as an app on the portable device and employed when using the treatment device 100. In some examples, the portable device can be interfaced to a wireless network and the control module 110 functions can be sent to the portable device. In some examples, the portable device can be interfaced to a wireless network and the portable device can be monitor over the wireless network. In some examples, the portable device can be interfaced to a wireless network and the portable device can upload data from treatments via the network.

The wireless or portable device can be configured to display an image generated by the treatment device 100. The wireless or portable device can be configured to control at least a portion of the treatment device 100. The wireless or portable device can be configured to store data generated by the treatment device 100 and sent to the wireless device.

In some configurations, the transducer module 150 can be configured as a roller, a cylinder, a sphere, or a combination thereof. In some configurations, the transducer module 150 can include an ultrasound transducer 162, a position sensor 240, a tissue contact sensor, a communication interface, the control module 110, a rechargeable power supply, an acoustic coupling medium dispenser 105, or any combination thereof. In certain configurations, the transducer module 150 can include at least two ultrasound transducers 162. The transducer module 150, the spherical transducer roller 190, and the roller ball module 179 can collectively be referred to as rolling members.

In certain configurations, the energy 170 can pass through at least one surface or wall of the rolling member. In certain configurations, the rolling member can be made of a number of materials that are temperature stable up to about 150° C. (for example, plastics and polymers) or to higher temperatures (for example, metals and alloys). In certain configurations, the rolling member can have material properties and a geometric shape to provide an ultrasound transmissive window having a thickness 154 that is a multiple of a half wavelength of the energy 170. In some configurations, the transducer module wall 151 can have a thickness 154 that is a half wavelength ("$\lambda$") of the energy 170 thick or is about a half wavelength of the energy 170 thick. In some configurations, the transducer module wall 151 can have a thickness 154 that is a multiple of a half wave length thick, such as, for example. multiples of 0, 1, 2, 3, . . . n of the half-wavelength. In certain configurations, the energy 170 can be an ultrasound energy, an photon-based energy, a radio-frequency energy, a microwave energy, or a combination thereof.

In some configurations, the energy source 160 can be configured with the ability to controllably produce conformal distribution of elevated temperature in soft tissue within the ROI 108 through precise spatial and temporal control of acoustic energy deposition. To this end, the control of energy source 160 may be configured within selected time and space parameters, with such control being independent of the tissue. The ultrasound energy 170 can be controlled to produce a conformal distribution of elevated temperature in soft tissue within ROI 108 using spatial parameters. The ultrasound energy 170 can be controlled to produce conformal distribution of elevated temperature in soft tissue within ROI 108 using temporal parameters. The ultrasound energy 170 can be controlled to produce a conformal distribution of elevated temperature in soft tissue within ROI 108 using a combination of spatial parameters and temporal parameters. In some configurations, a conformal distribution of elevated temperature in soft tissue within ROI 108 is conformal region of elevated temperature in ROI 108.

In various configurations, the energy source 160 can be configured to create an intensity gain from the energy source 160 to the ROI 108 of at least 100. Further, the energy source 160 can be configured to create an intensity gain from the target surface 106 to the ROI 108 of at least 5. In some configurations, the energy source 160 can be configured to focus the acoustic energy 170 into the ROI 108. As focused, the intensity from the energy source 160 to the ROI 108 can be in a range from 500 W/cm$^2$ to 25,000 W/cm$^2$. In some configurations, the energy source 160 can be configured to weakly focus the acoustic energy 170 into the ROI 108. As weakly focused, the peak intensity from the energy source 160 to the ROI 108 can be in a range from 5 W/cm$^2$ to 100 W/cm$^2$. The energy source 160 can be configured to focus the energy 170 into the ROI 108 to create an average intensity of at least 1000 W/cm$^2$ in the ROI 108. The energy source 160 can be configured to focus the energy 170 into the ROI 108 to create an intensity of at least 3 W/cm$^2$ at the target surface 106. The energy source 160 can be configured to focus the energy 170 into the ROI 108 to create an intensity of at least 10 W/cm$^2$ at the target surface 106.

In some configurations, the energy source 160 can be configured to direct the acoustic energy 170, which is defocused into the ROI 108. The energy source 160 can be configured to direct the acoustic energy 170, which is unfocused into the ROI 108. In some configurations, the energy source 160 can be configured to direct the acoustic energy 170 having a planar focus into the ROI 108.

The energy 170 can be emitted in a frequency in a range from 1 MHz to 30 MHz and for a time in a range from 1 nanosecond to 10 microseconds. Some configurations provide systems configured to direct the energy 170 into the ROI 108, which is emitted in a frequency in a range from 1 MHz to 2 GHz and for a time in a range from 100 picoseconds to 10 seconds. Some examples of these configurations provide systems configured to provide a power signal in a range of 1 kilowatt to 12 kilowatts to the energy source 160 to generate an amount of energy 170 in a range from 1 nanosecond to about 500 microseconds and in a range from about 0.5 milli-Joules to about 6 Joules, which is directed to the ROI 108. In some applications, the frequency range can be from 1 MHz to 30 MHz or can be from 1 MHz to 20 MHz or can be from 2 MHz to 10 MHz.

In many treatment applications, the frequency of the ultrasound energy 170 can be in a range from about 1 MHz to about 12 MHz, or from about 5 MHz to about 15 MHz, or from about 2 MHz to about 12 MHz or from about 3 MHz to about 7 MHz. In some applications, the frequency range can be from 1 MHz to 10 MHz or can be from 1 MHz to 7 MHz or can be from 2 MHz to 5 MHz.

The acoustic energy 170 can be emitted in an at least one increment in a range from 0.001 seconds to 5 seconds from the energy source 160 coupled to the target surface 106, wherein the acoustic energy 170 is emitted at a frequency in a range of 1 MHz to 20 MHz, at a peak intensity in a range of 5 W/cm2 to 70,000 W/cm2. The increment can be in a range from 0.001 seconds to 5 seconds is emitted repeatedly to deliver an amount acoustic energy necessary to provide a total amount of the medicant to achieve a clinical effect in the tissue. The increment can be in a range from 0.001 seconds to 5 seconds is emitted repeatedly with a delay of 10 microseconds to 1 second between each increment. The time length of time of an emission of the energy 170 into the ROI 108 for the domain of a thermal effect is in a range from milliseconds to minutes in a frequency range, as described above.

In some applications, the ultrasound energy 170 can create a thermal effect in the ROI 108. Since temperature in the ROI 108 is proportional to intensity of acoustic energy 170 that is delivered, providing a controlled delivery of the acoustic energy 170 into the ROI 108, which exceeds a thermal capacity of the medium (for example tissue) in the ROI 108, will damage or destroy the medium in the ROI 108. For example, a lesion can be created in subcutaneous tissue when the delivered ultrasound energy 170 exceeds the thermal capacity of the tissue. However, providing a controlled delivery of the acoustic energy 170 into the ROI 108, which increases the temperature in the ROI 108 of the medium but does not exceed a thermal capacity of the tissue can initiate a change of the tissue in the ROI 108 but does not destroy the tissue in the target zone of the ROI 108. For example, subcutaneous tissue can be heated to about 43 degrees C. to about 50 degrees C., which can cause the collagen to shrink but does not damage or destroy the tissue in the target zone.

In some configurations, the energy 170 can create a mechanical effect in the ROI 108. A mechanical effect is a non-thermal effect in a medium created by interaction with acoustic energy 170. A mechanical effect can be one of, for example, acoustic resonance, acousto-elastic effect, acousto-mechanical effect, acoustic streaming, disruptive acoustic pressure, shock waves, histrophy, inertial cavitation, and non-inertial cavitation.

At high enough acoustic intensities, cavitation is the formation of microbubbles in a liquid portion of the ROI 108. The interaction of ultrasound field with the microbubbles can cause the microbubbles to oscillate in the ROI 108 (non-inertial (dynamic) cavitation) or to grow and eventually implode (inertial cavitation). During inertial cavitation, very high temperatures inside the bubbles occur, and the collapse is associated with a shock wave that can mechanically damage the medium (such as tissue) in the ROI 108. The time length of time of an emission of the energy 170 for the domain of cavitation is in a range from microseconds to seconds in a frequency range, as described above. In some configurations, an overlap exists, in which both of the effects, the thermal effect and the cavitation effect can occur.

The acousto-mechanical effect can cause a micro-explosion in the target zone of the ROI 108. The acousto-mechanical effect can cause an increase in a pressure in the target zone above a threshold of fragmentation of the medium in the ROI 108. A fragmentation pressure is a minimum pressure at which a substance (for example a solid) in the ROI 108 of a particular medium will explode (shatter, fragment). The time length of time of an emission of the energy 170 for the domain of an acousto-mechanical effect is in a range from nanoseconds to microseconds in a frequency range, as described above. In some configurations, an overlap exists, in which both of the effects, the cavitation and the acousto-mechanical effect can occur.

The acousto-elastic effect is an effect in a medium that arises from the combination of the pressure oscillations of an acoustic wave with the accompanying adiabatic temperature oscillations in a target zone produced by the acoustic wave. Temperature of the surrounding medium in the ROI 108 is unchanged. The acousto-elastic effect is an effect in that can overcome threshold of elasticity of the molecules in the target zone of the ROI 108. The acousto-elastic effect increases the temperature from the inside out by thermal diffusion, which can dramatically increase temperature in a target zone thus resulting in a raise in pressure in the target zone.

The acousto-elastic effect can break the thermal elastic connection of the molecules in the target zone, which can cause a micro-explosion in the target zone of the ROI 108. The acousto-elastic effect can cause raise a temperature in the target zone above a fragmentation temperature of the medium in the target zone. A fragmentation temperature is a minimum temperature at which a substance (for example a solid) in the ROI 108 of a particular medium will explode (shatter, fragment). The time length of time of an emission of the energy 170 for the domain of an acousto-mechanical effect is in a range from picoseconds to microseconds in a frequency range, as described above. In some configurations, an overlap exists, in which both of the effects, the acousto-mechanical effect and the acousto-elastic effect can occur.

In some configurations, energy 170 can be ultrasound energy. In some configurations, the energy 170 can be more than one energy, for example, but not limited to ultrasound energy and a photon-based energy. Of course the energy 170 is not limited to only one energy or to two different energy types, for example, the energy 170 can include a number of energy types and/or can include a particular energy type at different frequencies. The energy source 160 can be configured to emit ultrasound energy. The energy source 160 can be configured to emit ultrasound energy and to emit a photon-based energy.

In some configurations, energy source 160 can be configured to emit at least two different forms of energy 170. For example, the energy source 160 can be configured to emit ultrasound energy into a portion of a treatment region and the energy source 160 can be configured to emit a second energy, which is different than ultrasound energy, into a portion of the treatment region. For example, the second energy can be provided by a laser, or an intense pulsed light (IPL), or a light emitting diode (LED), or a radio frequency source, or a microwave energy source, or a plasma source, or a magnetic resonance source, or a mechanical energy source, or any other photon-based energy source. In some applications, the energy source is a cryogenic source to provide treatment by cooling the targeted tissue. The second energy can be provided by any appropriate energy source now known or created in the future. The energy source 160 can be configured to emit a third energy, which can be provided by any source described herein. The energy source 160 can be configured to emit an nth energy, which can be provided by any source described herein.

In some configurations, the energy source 160 can include an ultrasound energy source and a photon-based energy source. For example, the photon-based energy source can be a laser. In some examples, the photon-based energy source can be IPL. In some examples, the photon-based energy source can be one or more LEDs. In some examples, the photon-based energy source can be a nanosecond Q-switch laser. In some examples, the photon-based energy source can be a picosecond Q-switch laser.

The photon-based energy source can be configured to emit "blue light" having a wavelength from about 400 nanometers to about 440 nanometers. Blue light may be applied as a pretreatment before the ultrasound energy is applied. Blue light may be applied concurrently with the ultrasound energy. The photon-based energy source can be configured to emit "red light" having a wavelength from about 600 nanometers to about 1350 nanometers. Red light may be applied as a pretreatment before the ultrasound energy is applied. Red light may be applied concurrently with the ultrasound energy. The photon-based energy source can be configured to emit ultraviolet (UV) energy having a wavelength from about 100 nanometers to about 400 nanometers. UV light may be applied as a pretreatment before the ultrasound energy is applied. UV light may be applied concurrently with the ultrasound energy.

In some configurations, the energy source 160 can include an ultrasound energy source and a RF energy source. In some configurations, the energy source 160 can include an ultrasound energy source and a microwave energy source. In some configurations, the energy source 160 can include an ultrasound energy source and a plasma source. In some configurations, the energy source 160 can include an ultrasound energy source and a magnetic resonance source energy source. In some configurations, the energy source 160 can include an ultrasound energy source and a mechanical energy source.

In some configurations, ultrasound energy 170 is a continuous wave emission. The transducer module 150 can couple the transducer 162 to ROI 108 and facilitates the transfer of the energy 170 from transducer 162 through any coupling medium 107 that is present and the transducer module wall 151 and into ROI 108. However, if the transducer module 150 is uncoupled from ROI 108 and is coupled to air, the transducer module wall can become a reflector and reflect all or at least a majority of the energy 170 back to transducer 162 as reflected energy.

In some configurations, a digital synthesizer can be coupled to transducer 162 and configured to frequency sweep transducer 162. In some configurations, frequency sweep can monitor the constant average output power of transducer 162. In some configurations, frequency sweep can be a step function of a set of different frequencies. In some configurations, the frequency sweep is a chirp function. In some configurations, the step function of a set of different frequencies can include a plurality of different frequencies.

Figure 22:
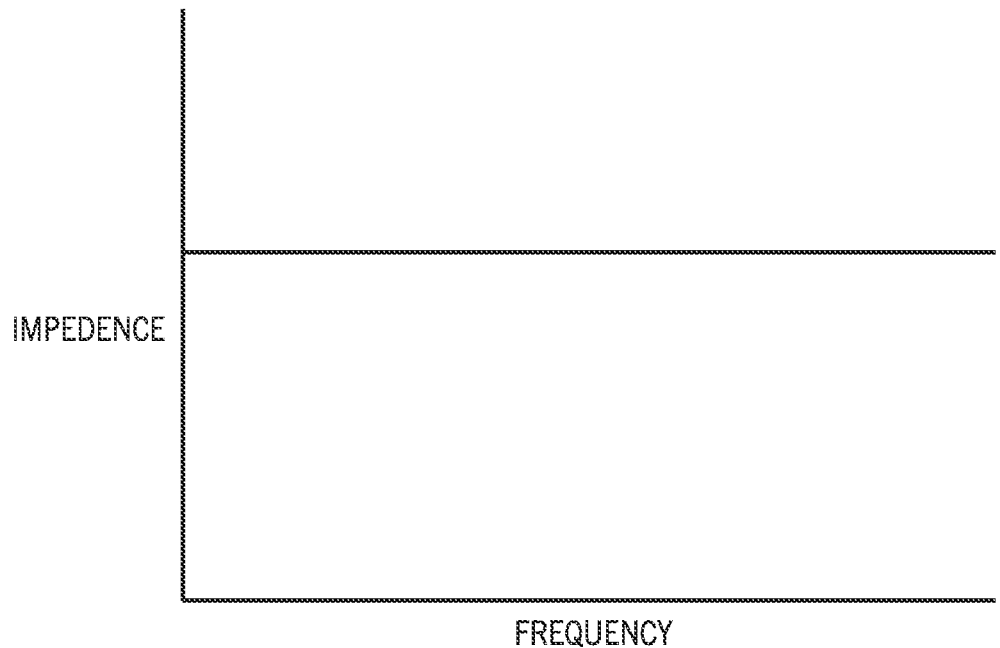
FIG. 22 is a graph illustrating resistance over time for an exemplary treatment coupled to tissue, according to one aspect of the present disclosure.
Figure 23:
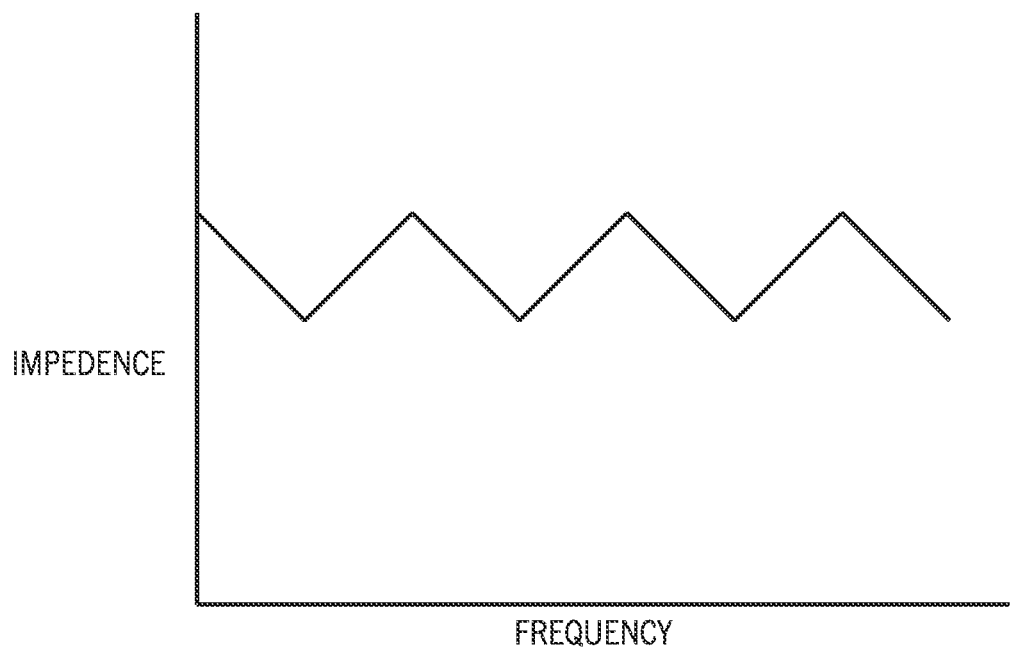
FIG. 23 is a graph illustrating resistance over time for an exemplary treatment not coupled to tissue, according to one aspect of the present disclosure.

In some configurations, an output from the frequency sweep can be monitored, as illustrated in FIGS. 22 and 23. The units for axis of the graphs in FIGS. 22 and 23 are electrical impedance in the y axis and frequency in the x axis. FIG. 22 illustrates the feedback from a frequency sweep when transducer module 150 is coupled to ROI 108. FIG. 23 illustrates the feedback from a frequency sweep when transducer module 150 is uncoupled (or coupled to air). This difference in feedback from the frequency sweep can be a coupling detection system. If the frequency sweep reports feedback is similar to FIG. 22 device 100 continues to function providing ultrasound energy 170 to ROI 108. If the frequency sweep reports feedback is similar to FIG. 23, the transducer 162 is shut down as a safety mechanism and/or to protect the transducer 162 from being damaged or destroyed.

In some configurations, the system can monitor and adjust output power to achieve a constant average output power, even with variations in the medium temperature and/or transducer temperature. In some configurations, the transducer module 150 can include a temperature sensor 242. In some configurations, transducer module 150 can include two temperature sensors 242. For example, one of the temperature sensors 242 can be in contact with coupling medium 107 and the second temperature sensor 242 can be in contact with transducer 162. In some configurations, if the temperature as reported by the temperature sensor is above, for example, 43 degrees C., the transducer 162 stops emission of ultrasound energy 170.

In certain configurations, the offset 181 can be used with the acoustic coupling medium dispenser 105, as discussed herein, to ensure the proper thickness of the coupling medium 107 is applied to the target surface 106. In some configurations, the acoustic coupling medium dispenser 105 can be integrated into the wheel 180. However, the acoustic coupling medium dispenser 105 can be placed in a variety of positions in system 100, as long dispenser 105 can provide coupling medium 107 to at least one of the transducer module 150 and the surface 106. The offset 181 can be used with a contact sensor, such as the contact sensors described herein, to provide coupling of the transducer 162 to the ROI 108 during use of the system 100.

In certain configurations, the position sensor 240 may be located behind a transducer, in front of a transducer array, or integrated into a transducer array. The ultrasound transducer module 150 may include more than one position sensor 240, such as, for example, a laser position sensor and a motion sensor, or a laser position sensor and a visual device, or a motion sensor and a visual device, or a laser position sensor, a motion sensor, and a visual device.

In some configurations, the position sensor 240 can include a visual element such as a camera or video capture device. In some configurations, the position sensor 240 can include a laser position sensor. In some configurations, the position sensor 240 can include a Doppler laser position sensor. In some configurations, the position sensor 240 can include a 3D magnetic sensor. For example, an optical position sensor can track position like a computer mouse that uses a laser sensor as opposed to an older version of a mouse with a roller ball. The position sensor can communicate position data versus time to a display to track a position of ultrasound transducer module 150, such as, for example, overlaid on an image of ROI 108, overlaid on an image of target surface 106, as referenced to tagged or pre-identified features, as reference to injury location, as referenced to a prior treatment, and combinations thereof. In an exemplary configuration, a treatment plan can include a movement pattern of ultrasound transducer module 150. Such a movement pattern can be displayed and the position sensor can track a position of ultrasound transducer module 150 during treatment as compared to the movement pattern. Tracking the ultrasound transducer module 150 with position sensor and comparing the tracked movement to a predetermined movement may be useful as a training tool. In some configurations, laser position sensor can tag or identify a feature on target surface 106.

In some configurations, the position sensor 240 may determine a distance between pulses of therapeutic ultrasound energy 170 to create a plurality of treatment zones that are evenly spaced or disposed in any spatial configuration in 1-D or 2-D patterns. As the ultrasound transducer module 150 is moved in a direction 104, the position sensor 240 can determine distance, regardless of a speed that ultrasound transducer module 150 is moved, at which a pulse of therapeutic ultrasound energy 170 is to be emitted in to ROI 108.

In some configurations, the transducer module 150 can include a contact sensor 244. In some configurations, the contact sensor 244 can communicate whether the transducer module 150 is coupled to the ROI 108. The contact sensor 244 may measure a capacitance of a target surface 106 above the ROI 108 and communicate a difference between the capacitance of the contact to the target surface 106 and the capacitance of air. In some configurations, the tissue contact sensor can be initiated or turned on by pressing the ultrasound transducer module 150 against the target surface 106.

In various configurations, the transducer module 150 can include a contact sensor 244. In some configurations, the contact sensor 244 can communicate whether transducer module 150 is coupled to the ROI 108. The tissue contact sensor may measure a capacitance of a target surface 106 above the ROI 108 and communicate a difference between the capacitance of the contact to the target surface 106 and the capacitance of air. In some configurations, the tissue contact sensor is initiated or turned on by pressing ultrasound probe against target surface 106.

Various configurations provide methods of sensing coupling of an ultrasound source 162 to a ROI 108. For example, a method of sensing coupling includes providing the energy source 160 having the transducer 162, providing the transducer module 150 having a substantially curved outer surface with a thickness 154 of about one-half wavelength of the acoustic energy and configured to encase the transducer 162 and a coupling medium, and performing a frequency sweep function. The method can include emitting ultrasound energy 170 from the transducer 162; receiving reflected energy 170; frequency sweeping the transducer; determining the feedback from the frequency sweep is below (or above depending where the level is set) a threshold level; and determining if the transducer 162 is coupled to the ROI 108.

In some configurations of the method, if the feedback from the frequency is above the threshold level, then the transducer 162 is not coupled to the ROI 108. In some configurations, if the feedback from the frequency is above (or below depending where the level is set) the threshold level, then the transducer 162 is coupled to the ROI 108. The method can further include providing constant average output power from the transducer 162. The method can further include terminating power to the transducer 162. The sweep frequency has a period, which is calculated using a path length of the standoff and the speed of sound.

Various configurations provide a contact sensor 244 for determining whether an ultrasound source 160 is coupled to a target 108. In some configurations, the coupling sensing system includes an ultrasound source 160 having a transducer 162, an acoustically transparent standoff (transducer module 150) coupled to the transducer 162 including a substantially curved outer surface having a thickness 154 of about one-half wavelength of the acoustic energy at a bottom surface of the standoff. The substantially curved outer surface having a thickness 154 of about one-half wavelength is a reflector when the ultrasound source 162 is not coupled to the ROI 108. The substantially curved outer surface having a thickness 154 of about one-half wavelength is transparent to ultrasound energy 170 when the ultrasound source 162 is coupled to the ROI 108.

In various configurations, the contact sensor 244 can be combined with one or more different sensing techniques. For example, the contact sensor 244 can be combined with a hall detector. For example, the contact sensor 244 can be combined with an optical detector. For example, the contact sensor 244 can be combined with a conductive detector. For example, the contact sensor 244 can be combined with a piezo electric detector. For example, the contact sensor 244 can be combined with a mechanical detector. For example, the contact sensor 244 can be combined with a magnetic detector. In various configurations, the coupling detection system can be combined with at least one of a hall detector, optical detector, an acoustic impedance detector, a conductive detector, a piezo electric detector, a mechanical detector, a magnetic detector, an acoustic impedance detector, and combinations thereof.

Figure 24:
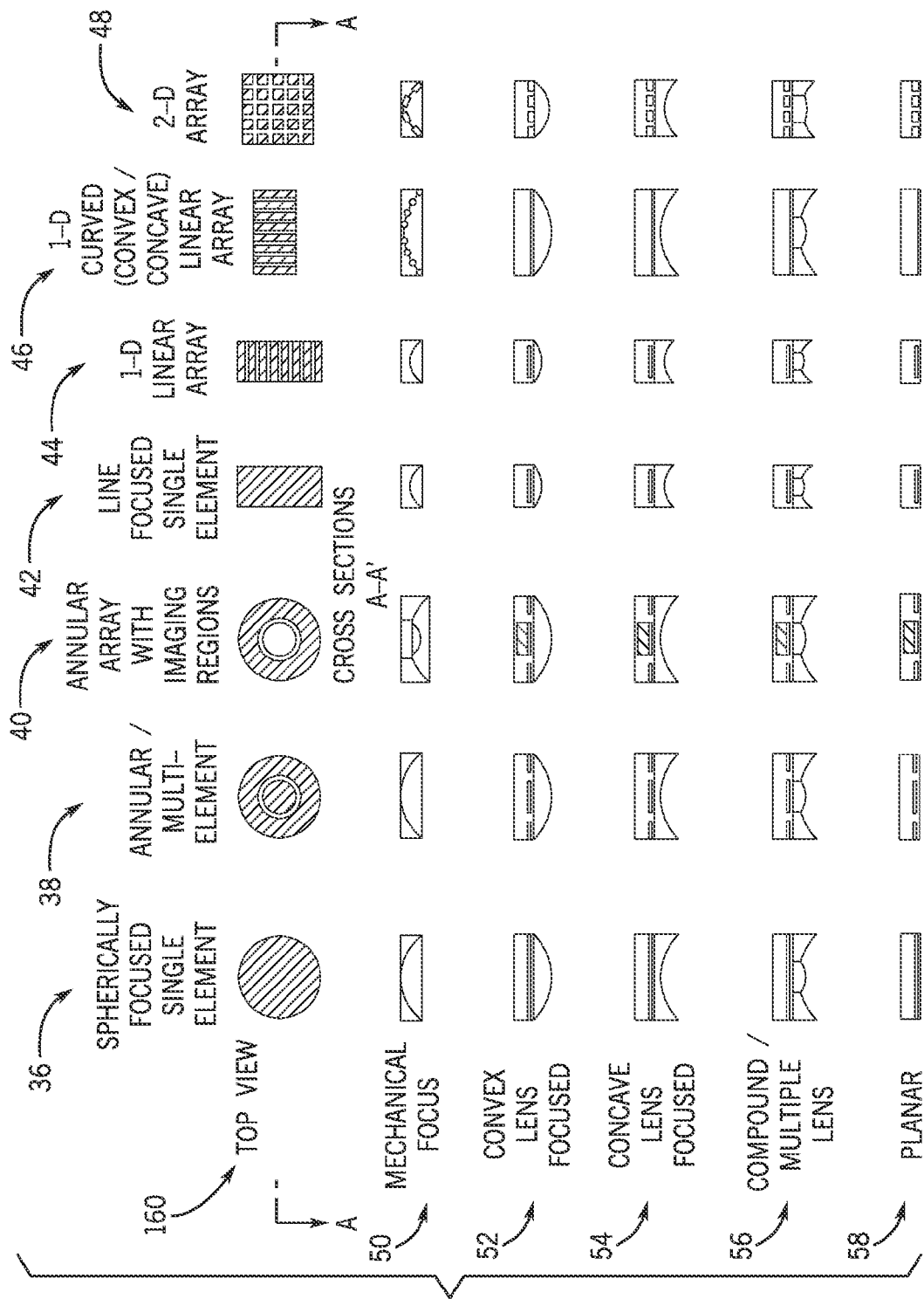
FIG. 24 is a matrix diagram illustrating a variety of transducer and lens configurations, according to one aspect of the present disclosure.

Referring to FIG. 24, a plurality of exemplary energy source 160 configurations is illustrated in accordance with various configurations. In some configurations, the energy source 160 includes at least one ultrasound transducer 162. In some configurations, energy source 160 includes at least one ultrasound transducer and a focusing device 164, such as, for example, a lens.

For example, a transducer 162 may include a spherically focused single element 36. The transducer 162 may include an annular/multi-element array 38. The transducer 162 may include an annular array with an imaging region 40. A transducer 162 may include a line-focused single element array 42. The transducer 162 may include a 1-D linear array 44. The transducer 162 may include a 1-D curved (convex or concave) linear array 46. The transducer 162 may include a 2-D array 48.

With further reference to FIG. 24, the previous described configurations of a transducer 162 can be coupled to a lens 164. For example, the lens 164 can be a mechanical focus lens 50. the lens 164 can be a convex focus lens 52. The lens 164 can be a concave focus lens 54. The lens 164 can be a compound/multiple focused lens 56. The lens 164 can be a planar lens 58. The transducer 162 may be individually or in combination coupled to a lens 164 to provide at least one of a focused ultrasound energy 170, an unfocused ultrasound energy 170, or a defocused ultrasound energy 170.

Figure 25:
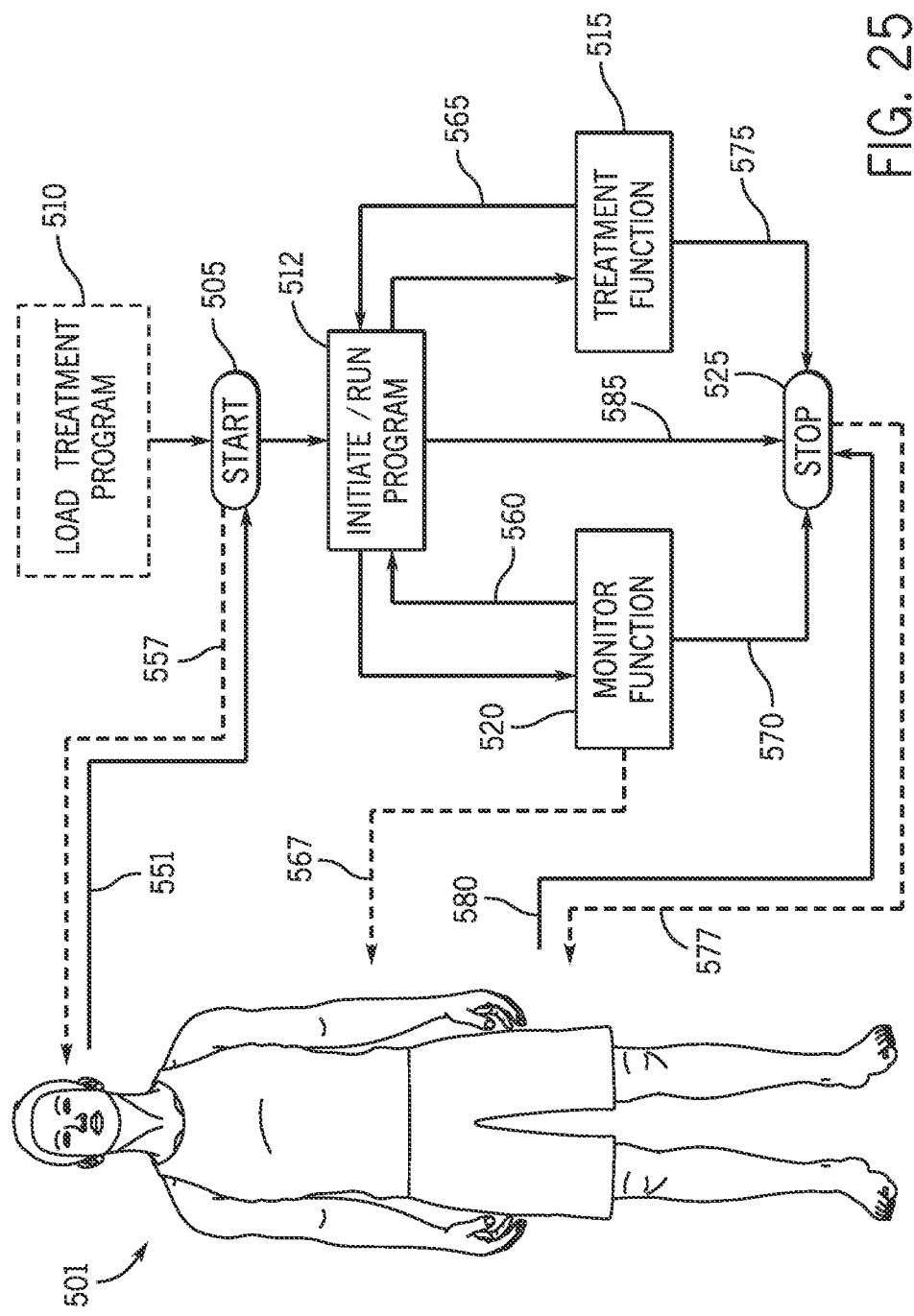
FIG. 25 is a flowchart illustrating exemplary methods, according to one aspect of the present disclosure.

Moving to FIG. 25, a flow chart illustrates an exemplary operation of the treatment system, according to various configurations. The process includes a treatment start 505 and a treatment stop 525. A treatment program 510 can be loaded into the control module 110 to start the process 505. The treatment program 510 can be loaded during manufacture of the treatment device 100, which locks the device 100 into only the provided treatment program 510. However, the treatment program 510 may be selected by user 501. The treatment program 510 instructs the control module 110 to provide programmed distribution of energy 170 in the ROI 108 for the desired treatment. The treatment program 510 can include parameters for the treatment function 515.

To use the treatment device 100, the user 501 interfaces 551 with the treatment device 100 to provide a treatment start signal 505 that initiates and/or run the treatment program 510 and provides open-loop feedback 557 to the user 501 that treatment has started, such as, a signal or an indicator, which could be, for example, a lit LED or a message on a screen.

As the treatment device 100 runs treatment program 512, the control module 110 operates a monitor function 520, which provides closed-loop feedback 560 with the treatment program 512. If feedback 560 is provided to indicate a positive signal, the run treatment program 512 continues. If the feedback 560 provides a negative signal, a stop signal 525 is sent to the control module 110 and the treatment program 512 is terminated. To this end, the system may provide closed-loop feedback and control. The monitor function 520 can also provide an open-loop feedback 567 to the user 501, which may include a system ready indication, a system operating within programmed parameters indication, and/or a system fault indication. For example, such feedback 567 may be communicated by, for example, LEDs and/or in text or symbol format displayed on a screen of the treatment device 100 or in communication with the treatment device 100 or mobile device, such as, for example a smart phone or a tablet device.

The monitor function 520 can monitor temperature of the transducer module 150 and relative to a threshold. The monitor function 520 can monitor battery power and provide a lower threshold. The monitor function 520 can monitor a number of lines of treatment provided by energy source 160 and provide a threshold, which is an upper limit of the number lines. The monitor function 520 can monitor a total use time and provide a time threshold. The monitor function 520 can monitor the treatment system electronics and or mechanics and provide a fault signal. The monitor function 520 can monitor any other operational parameter or basic safety parameter and provide a positive or negative signal based on the parameter status via the closed-loop feedback 560. Thus, the monitor function 520 can monitor the operation of the device 100, including treatment parameters and non-treatment parameters. The threshold or limit provides a decision point for the monitor function 520.

Various sensing and monitoring components may also be implemented within the monitoring function 520. For example, the monitoring function 520 may be capable of operating with various motion detection systems implemented within treatment device 100, to receive and process information such as acoustic or other spatial and temporal information from ROI 108. The monitoring function 520 may also include various controls, interfacing, and switches and/or power detectors.

In some configurations, the monitoring function 520 may further include a sensor that may be connected to an audio or visual alarm system to prevent overuse of system. For example, the sensor may be capable of sensing the amount of energy transferred to the skin, and/or the time that the treatment device 100 has been actively emitting energy 170. When a certain time or temperature threshold has been reached, the monitor function 520 can provide an open-loop feedback 567 to alert the user 501 that the threshold has been reached, which may include one of more of an audible alarm, a visual indicator, or an alphanumeric message. The threshold can be used to control overuse of treatment device 100. The monitoring function 520 can provide closed-loop feedback 560, such as, for example, the sensor may be operatively connected to control module 110 and force control module 110, to stop emitting ultrasound energy 170 from ultrasound transducer module 150. In some configurations that include the coupling medium application device 105, the empty sensor 277 can provide an open-loop feedback 275 to the monitor function 520 and the control module 110.

As the treatment device 100 runs treatment program 512, the control module 110 can operate a treatment function 515, which provides closed-loop feedback 560 with the treatment program 512. If closed-loop feedback 565 provides a positive signal, the treatment program 512 continues. If the closed-loop feedback 565 provides a negative signal, a stop signal 525 is sent to the control module 110 and the treatment program 512 is terminated. The treatment function 515 can utilize the treatment parameters and thresholds, which provide closed-loop feedback, which can be either positive or negative signals based on the thresholds. If a treatment parameter of the treatment function 515 goes over the threshold or limit, a stop treatment signal 525 and the control module 110 terminates the treatment program 512.

For example, treatment function 515 can provide the control module 110 the parameters of movement of the transducer module 150. For example, parameters of movement, such as, a minimum speed, a maximum speed, and/or a change of direction, may be included in the treatment function 515. The treatment function 515 can provide spatial parameters and/or temporal parameters of the energy source 160, to provide a programmed distribution of energy 170 in the ROI 108. If the system is not operating within these parameters, a stop treatment signal 525 and the control module 110 can terminate the treatment program 512. The treatment function 515 can send a stop signal 585 at the end of the programmed treatment. The end of the programmed treatment maybe based on a time period, a total amount of energy delivered, or a total amount of area treated, or any combination thereof.

If the stop 525 has been initiated by either the monitor function 520, the treatment function 515, or the user 501, an open-loop feedback 577, such as, a stop indicator is communicated to the user 501. The user 501 can interface 580 with the treatment device 100 to send a stop signal 525 to control module 110.

In an example, the control module 110 is configured to receive at least one communication and control a distribution of the acoustic energy 170 transmitted by the transducer 162. A coupling sensing system, in communication with the control module 110, can be configured to determine whether the transducer 162 is coupled to the ROI 108 by monitoring an amount of reflection of the acoustic energy 170 back to the transducer 162 by the outer surface 152 of the module wall 151, which has a thickness 154 of about one-half wavelength. The position sensor 240, in communication with the control module 110, can be configured to monitor the speed of rotation of the transducer module 150. A treatment function 515 can be configured to send a positive signal the control module 110 via closed-loop feedback 565, if the coupling sensing system communicates the transducer 162 is coupled to the ROI 108, and if the speed of the rotation of the transducer module 150 is greater than a programmed minimum speed or is less than a programmed maximum speed.

The treatment function 515 can further be configured to send a positive signal the control module 110 via closed-loop feedback 565, if the speed of the rotation of the transducer module 150 is above a minimum speed. The treatment function 515 can further be configured to send a positive signal the control module 110 via closed-loop feedback 565, if the speed of the rotation of the transducer module 150 is below a maximum speed. The treatment function 515 can further be configured to send a positive signal the control module 110 via closed-loop feedback 565, if the direction of the rotation of the transducer module 150 is unchanged.

The treatment function 515 can further be configured to send a stop signal 525 to the control module 110, if the coupling sensing system communicates the transducer 162 is not coupled to the ROI 108. The treatment function 515 can further be configured to send a stop signal 525 to the control module 110, if the speed of the rotation of the transducer module 150 is below the minimum speed. The treatment function 515 can further be configured to send a stop signal 525 to the control module 110, if the speed of the rotation of the transducer module 150 is above the maximum speed. The treatment function 515 can further be configured to send a stop signal 525 to the control module 110, if the direction of the rotation of the transducer module 150 has changed.

In an example, the treatment program 512 can be configured to initiate the treatment stop command 525 after the transducer module 150 and the portion of the treatment device 100, as reported by the second position sensor move a programmable and defined distance. The treatment device 100 can be configured to maintain the distribution of the acoustic energy 170 into the ROI 108, if the coupling sensing system communicates the transducer 162 is coupled to the ROI 108, and if the first position sensor 240 and the second position sensor communicate the movement of the transducer module 150 is substantially similar to the movement of the portion of the treatment device 100, as reported by the second position sensor.

In an example, the treatment program 512 can be initiated by the treatment start command 505 configured to signal the control module 110 to initiate the distribution of the acoustic energy 170 into the at least one of the target surface 106 and the ROI 108. The treatment stop command 525 causes the control module 110 to terminate the distribution of the acoustic energy 170 into the at least one of the target surface 106 and the ROI 108. The treatment function 515 can be configured to initiate the treatment stop command, if the coupling detector communicates the transducer 162 is not coupled to the ROI 108, or if the speed of the transducer module 150 along the surface 106 is substantially different than the speed reported by the second position sensor, or if the position of the transducer module 150 is substantially different than the position reported by the second position sensor.

In an example, the treatment program 512 can be configured to maintain the distribution of the acoustic energy 170 into the ROI 108, if the speed of the transducer module 150 is above a minimum speed. The treatment device 100 can be configured to maintain the distribution of the acoustic energy 170 into the ROI 108, if the speed of the transducer module 150 is below a maximum speed. The treatment program 512 can be configured to maintain the distribution of the acoustic energy 170 into the ROI 108, if a direction of the rotation of the transducer module 150 is unchanged. In an example, the treatment program 512 can be configured to maintain the distribution of the acoustic energy 170 into the at least one of the target surface 106 and the ROI 108, if the coupling sensing system communicates the transducer 162 is coupled to at least one of the target surface 106 and the ROI 108, and if the speed the rotation of the transducer module 150 is below the maximum speed.

As used above, "substantially different" can be a difference of at least 10%-15%. However, at slower speeds of the wheels, substantially different can be a difference of at least 5%, However, with the use of digital position sensors and/or 128 position stepper devices, substantially different can be a difference of at least 2% or less, such as at least 1%. Substantially similar can be a difference of less than 10%-15%. However, at slower speeds of the wheels, substantially similar can be a difference of less than 5%. However, with the use of digital position sensors and/or 128 position stepper devices, substantially similar can be a difference of less than 2% or less, such as less than 1%. The actual percentage for the difference is limited by the accuracy of the position sensors, which are used in the treatment device 100. Position sensors with better accuracy allow for lower percentages for the differences. In an example of a movement of the device 100 having slow speed of 1 cm/sec, the difference of 15% (1.5 mm) may be acceptable. However, as speeds increases, the percentage of the difference needs to be lower and more accurate positions sensors are used. The accepted difference is based on the speed of the movement of the device 100 and the pitch of the treatment lines created by the energy 170.

Some configurations provide a method configured for treating a desired ROI including a target volume below large area of target surface 106. For example, the ROI can be at least a portion of the legs and buttocks during a treatment. For example, the ROI can be at least a portion of midsection during a treatment. Some configurations provide a treatment device 100 configured to treat a large surface area 106 and includes a plurality of transducer modules 150, each of which are coupled to a control module 110.

In some configurations, the method can further include initiating at least one thermal effect in the ROI 108. The at least one thermal effect is the thermal effect is one of heating in the ROI 108, or creating a conformal region of elevated temperature in the ROI 108. In some configurations, the thermal effect is one of lesion creation in the ROI 108, tissue necrosis in a portion of the ROI 108; coagulation tissue in the ROI 108, or exceeding a thermal capacity of tissue in a portion of the ROI 108, and combinations thereof.

In some configurations, the method can further include initiating at least one mechanical effect in the ROI 108. The at least one mechanical effect is at least one of cavitation, vibration, hydrodynamic, resonance-induced, streaming, vibro-accoustic stimulation, a pressure gradient and combinations thereof.

In some configurations, the method can further include providing at least one biological effect in the ROI 108 based in the temperature function. The at least one biological effect can be destroying tissue in the at least a portion of the ROI 108.

In some configurations, the method can further include monitoring of results of the acoustic tissue treatment during the delivery of acoustic energy 170. The method can further include monitoring of results of the acoustic tissue treatment after the delivery of acoustic energy 170. The method can further include planning of additional treatment.

The above-described roller design is particularly useful for larger body areas such as treatment of cellulite/fat in hips and buttocks or treatment of the abdomen. However, a smaller roller design could be useful in treatments on the face or other areas with a smaller surface or treatment area.

The present invention has been described above with reference to various exemplary configurations. However, those skilled in the art will recognize that changes and modifications may be made to the exemplary configurations without departing from the scope of the present invention. For example, the various operational steps, as well as the components for carrying out the operational steps, may be implemented in alternate ways depending upon the particular application or in consideration of any number of cost functions associated with the operation of the system, e.g., various of the steps may be deleted, modified, or combined with other steps. Further, it should be noted that while the method and system for ultrasound treatment as described above is suitable for use by a medical practitioner proximate the patient, the system can also be accessed remotely, i.e., the medical practitioner can view through a remote display having imaging information transmitted in various manners of communication, such as by satellite/wireless or by wired connections such as IP or digital cable networks and the like, and can direct a local practitioner as to the suitable placement for the transducer. Moreover, while the various exemplary embodiments may comprise non-invasive configurations, system can also be configured for at least some level of invasive treatment application. These and other changes or modifications are intended to be included within the scope of the present invention, as set forth in the following claims.

The invention claimed is:

1. A treatment device for delivering a therapeutic ultrasound energy into a region of interest beneath a target surface, the treatment device comprising:
   a therapeutic ultrasound energy source configured for delivery of the therapeutic ultrasound energy;
   a rolling member to move the treatment device relative to the target surface, the rolling member comprising a wall disposed between the therapeutic ultrasound energy source and the region of interest, the therapeutic ultrasound energy passing through the wall at least once prior to the delivery into the region of interest;
   a plurality of parallel friction strips affixed to an outer surface of the rolling member;
   an ultrasound controller configured to control the therapeutic ultrasound energy source;
   a contact sensor in communication with the ultrasound controller and configured to determine when the therapeutic ultrasound energy source is acoustically coupled to the region of interest by identifying energy reflected back toward the therapeutic ultrasound energy source that is one half wavelength of the therapeutic ultrasound energy or a simple multiple of one half wavelength of the therapeutic ultrasound energy; and
   a housing coupled to the rolling member to move along the target surface while retaining acoustic coupling between the therapeutic ultrasound energy source and the region of interest,
   wherein the therapeutic ultrasound energy source is positioned within the rolling member,
   wherein the wall has a thickness of one half wavelength of the therapeutic ultrasound energy or a simple multiple of one half wavelength of the therapeutic ultrasound energy,
   wherein the therapeutic ultrasound energy source is reflected by the wall when the therapeutic ultrasound energy source is uncoupled from the region of interest, which signals the ultrasound controller to terminate the delivery of the therapeutic ultrasound energy.

2. The treatment device according to claim 1, wherein the rolling member is sealed and contains a coupling medium to facilitate coupling of the therapeutic ultrasound energy source with the region of interest.

3. The treatment device according to claim 1, wherein the therapeutic ultrasound energy source is at least one ultrasound transducer configured to controllably direct acoustic energy into the region of interest.

4. The treatment device according to claim 1, wherein the therapeutic ultrasound energy source comprises at least one ultrasound transducer configured to controllably direct acoustic energy into the region of interest and the treatment device further comprises a second energy source configured to provide energy, other than acoustic energy, to the region of interest.

5. The treatment device according to claim 1, the treatment device further comprising a position sensor in communication with the ultrasound controller and configured to monitor a position of the treatment device or to calculate a speed of the treatment device.

6. The treatment device according to claim 5, wherein the ultrasound controller terminates the delivery of the therapeutic ultrasound energy if the position of the treatment device is outside a pre-defined area of treatment or if the speed of the treatment device is greater than an upper threshold.

7. The treatment device according to claim 1, the device further comprising an axle positioned through a center axis of the rolling member.

8. The treatment device according to claim 1, the contact sensor comprising a hall detector, an optical detector, an acoustic impedance detector, a conductive detector, a piezo electric detector, a mechanical detector, a magnetic detector, a capacitive detector, or a combination thereof.

9. The treatment device according to claim 1, the treatment device further comprising one or more lenses.

10. The treatment device according to claim 1, wherein the target surface is a skin surface.

11. The treatment device according to claim 1, wherein the region of interest is a subcutaneous region of interest.

12. A method of treating a first location and a second location within a region of interest beneath a target surface by delivery of a therapeutic ultrasound energy, the method comprising:
  a) transmitting the therapeutic ultrasound energy, provided by a therapeutic ultrasound energy source of a treatment device, through at least one wall of a rolling member of the treatment device and into the first location, the rolling member having a plurality of parallel friction strips affixed to an outer surface of the rolling member;
  b) sensing, using a contact sensor of the treatment device, a coupling between the therapeutic ultrasound energy source and the region of interest by identifying energy reflected back toward the therapeutic ultrasound energy source that is one half wavelength of the therapeutic ultrasound energy or a simple multiple of one half wavelength of the therapeutic ultrasound energy;
  c) moving the treatment device relative to the target surface; and
  d) either:
  terminating the therapeutic ultrasound energy transmission if the coupling between the therapeutic ultrasound energy source and the region of interest is interrupted; or
  transmitting the therapeutic ultrasound energy, provided by the therapeutic ultrasound energy source, through the at least one wall of the rolling member and into the second location if the coupling between the therapeutic ultrasound energy source and the region of interest is uninterrupted,
  wherein the therapeutic ultrasound energy source is positioned within the rolling member,
  wherein the wall has a thickness of one half wavelength of the therapeutic ultrasound energy or a simple multiple of one half wavelength of the therapeutic ultrasound energy,
  wherein the therapeutic ultrasound energy source is reflected by the wall when the therapeutic ultrasound energy source is uncoupled from the region of interest, which signals the ultrasound controller to terminate the delivery of the therapeutic ultrasound energy.

13. The method according to claim 12, wherein the rolling member is sealed and contains a coupling medium to facilitate coupling between the therapeutic ultrasound energy source and the region of interest.

14. The method according to claim 12, the method further comprising monitoring, using a position sensor of the treatment device, a position of the treatment device relative to the target surface or a speed of the treatment device relative to the target surface.

15. The method according to claim 14, wherein step d) comprises either:
  terminating the therapeutic ultrasound energy transmission if the coupling between the therapeutic ultrasound energy source and the region of interest is interrupted, if the position of the treatment device is outside a pre-defined area of treatment, or if the speed of the treatment device is greater than an upper threshold; or
  transmitting the therapeutic ultrasound energy, provided by the therapeutic ultrasound energy source, through the at least one wall of the rolling member and into the second location if the coupling between the therapeutic ultrasound energy source and the region of interest is uninterrupted, the position of the treatment device is inside the pre-defined area, and the speed of the treatment device is less than the upper threshold.

16. The method according to claim 12, wherein the target surface is a skin surface.

17. The method according to claim 12, wherein the region of interest is a subcutaneous region of interest.

18. A treatment device for delivering an energy into a region of interest beneath a target surface, the treatment device comprising:
  an energy source configured for delivery of the energy;
  a rolling member to move the treatment device relative to the target surface, the rolling member comprising a wall disposed between the energy source and the region of interest, the energy passing through the wall at least once prior to the delivery into the region of interest;
  a plurality of parallel friction strips affixed to an outer surface of the rolling member;
  an energy source controller configured to control the energy source;
  a sensor in communication with the energy source controller and configured to determine when the energy source is coupled to the region of interest by identifying energy reflected back toward the energy source that is one half wavelength of the energy or a simple multiple of one half wavelength of the energy; and
  a housing coupled to the rolling member to move along the target surface while retaining coupling between the energy source and the region of interest,
  wherein the energy source is positioned within the rolling member,
  wherein the wall has a thickness of one half wavelength of the energy or a simple multiple of one half wavelength of the energy,
  wherein the energy source is reflected by the wall when the energy source is uncoupled from the region of interest, which signals the energy source controller to terminate the delivery of the energy.

19. The treatment device of claim 18, wherein the energy is a therapeutic ultrasound energy or the energy source is a therapeutic ultrasound energy source.

20. The treatment device of claim 18, the treatment device further comprising a position sensor in communication with the energy source controller and configured to monitor a position of the treatment device or to calculate a speed of the treatment device.

21. The treatment device of claim 20, wherein the energy source controller terminates the delivery of the energy if the position of the treatment device is outside a pre-defined area of treatment or if the speed of the treatment device is greater than an upper threshold.

\* \* \* \* \*